(12) United States Patent
Karstens et al.

(10) Patent No.: US 8,017,782 B2
(45) Date of Patent: *Sep. 13, 2011

(54) 4-PHENYL-5-OXO-1,4,5,6,7,8-HEXAHYDRO QUINOLINE DERIVATIVES AS MEDICAMENTS FOR THE TREATMENT OF INFERTILITY

(75) Inventors: Willem Frederik Johan Karstens, Oss (NL); Cornelis Marius Timmers, Oss (NL)

(73) Assignee: N.V. Organon, Oss (NL)

( * ) Notice: Subject to any disclaimer, the term of this patent is extended or adjusted under 35 U.S.C. 154(b) by 890 days.

This patent is subject to a terminal disclaimer.

(21) Appl. No.: 11/912,756

(22) PCT Filed: May 2, 2006

(86) PCT No.: PCT/EP2006/061978
§ 371 (c)(1),
(2), (4) Date: Oct. 26, 2007

(87) PCT Pub. No.: WO2006/117371
PCT Pub. Date: Nov. 9, 2006

(65) Prior Publication Data
US 2008/0262033 A1    Oct. 23, 2008

(30) Foreign Application Priority Data
May 4, 2005   (EP) .................................. 05103741

(51) Int. Cl.
*C07D 215/04* (2006.01)
*C07D 215/00* (2006.01)
*C07D 413/00* (2006.01)
(52) U.S. Cl. ................... 546/173; 546/165; 544/128
(58) Field of Classification Search ............... 546/165, 546/173; 544/128
See application file for complete search history.

(56) References Cited

U.S. PATENT DOCUMENTS

| | | | |
|---|---|---|---|
| 5,455,253 A * | 10/1995 | Ohnmacht et al. | 514/311 |
| 5,622,964 A * | 4/1997 | Ohnmacht et al. | 514/311 |
| 6,087,503 A | 7/2000 | Furuya et al. | |
| 6,194,428 B1 | 2/2001 | Urbahns et al. | |
| 2008/0275042 A1 | 11/2008 | Poveda et al. | |
| 2008/0300270 A1 | 12/2008 | Timmers et al. | |
| 2009/0215773 A1 | 8/2009 | Van Straten et al. | |

FOREIGN PATENT DOCUMENTS

| | | |
|---|---|---|
| DE | 1070162 | 12/1959 |
| EP | 0 755 931 | 1/1997 |
| JP | 2003026630 | 1/2003 |
| WO | WO 94/08966 | 4/1994 |
| WO | WO 96/06610 | 3/1996 |
| WO | WO 00/08015 | 2/2000 |
| WO | WO 00/78768 | 12/2000 |
| WO | WO 02/09706 | 2/2002 |
| WO | WO 03/004028 | 1/2003 |
| WO | WO 2004/056779 | 7/2004 |

OTHER PUBLICATIONS

Altmayer, et al., "Propofol Binding to Human Blood Proteins", *Arzneim.-Forsch./Drug Res.* (1995) 45: 1053-1056.
Anelli et al., "Smiles Rearrangement as a Tool for the Preparation of 5-[(2-Hydroxyacyl)amino]-2,4,6-triiodo-1,3-benzenedicarboxamides: Main Pathway and Side Reactions," *Tetrahedron* (1997) 53:11919-11928.
Aranyos, et al., "An Application of the Stille Coupling for the Preparation of Arylated Phthalonitriles and Phthalocyanines", *Acta Chem. Scand.* (1999) 53: 714-720.
Bahner, et al., "Halogenated Aminobenzaldehydes and Aminostyrylquinolines", *J. Org. Chem*, 25 (1960) 2053-2055.
Baker, William R. "Alkoxide-Accelerated Smiles Rearrangements. Synthesis of N-(2-Hydroxyethyl)anilines from N-(2-Hydroxyethyl) (aryloxy)acetamides," *J. Org. Chem.* (1983) 48: 5140-5143.
Bierbaum et al., "Hypotensive 1,2,4-Benzothiadiazines," *J. Med. Chem.* (1963) 6: 272-275.
Claiborne et al., "Orally Efficacious NR2B-Selective NMDA Receptor Antagonists," *Bioorg. & Med. Chem. Lett*. 13:697-700, 2003.
Crich, et.al., "Enantiospecific Synthesis with Amino Acids. Part 2. a-Alkylation of Tryptophan: A Chemical and Computational Investigation of Cyclic Tryptophan Tautomers", *J. Chem. Soc. Perkin Trans*. 2 (1992) 2233-2240.
Devroey, et al., "Successful in-vitro fertilisation and embryo transfer after treatment with recombinant human FSH", *Lancet* 339 (1992) 1170-1171.
Dondoni et al., "Two- and Three-Component Hantzsch Reaction Using C-Glycosylated Reagents. Approach to the Asymmetric Synthesis of 1,4-Diyhydropyridines", *Synlett* (2002) 89-92.
Dorrington & Armstrong, "Effects of FSH on Gonadal Functions", *Recent Prog. Horm. Res*., 35 (1979) 301-342.

(Continued)

*Primary Examiner* — Nizal Chandrakumar
(74) *Attorney, Agent, or Firm* — Janet E. Fair; John C. Todaro

(57) ABSTRACT

The present invention relates to 2-methyl-4-phenyl-5-oxo-1, 4,5,6,7,8-hexahydroquinoline derivatives having the general Formula (I) wherein the substituents are defined as in the description, or a pharmaceutically acceptable salt thereof. The invention also relates to pharmaceutical compositions comprising said derivatives, as well as to the use of these 2-methyl-4-phenyl-5-oxo-1,4,5,6,7,8-hexahydroquinoline derivatives in therapy, more specifically for the treatment of fertility disorders.

7 Claims, 1 Drawing Sheet

(I)

OTHER PUBLICATIONS

Dow, et al., "Discovery of a Novel Series of 6-Azauracil-Based Thyroid Hormone Receptor Ligands:Potent, TRβ Subtype-Selective Thyromimetics", *Bioorg. & Med. Chem. Lett.* 13 (2003) 379-382.

Drizin, et al., "Structure-Activity Studies for a Novel Series of Tricyclic Dihydropyrimidines as KATP Channel Openers (KCOs)", *Bioorg. & Med. Chem. Lett.* 12 (2002) 1481-1484.

Eisner, et al., "The Chemistry of Dihydropyridines", *Chem. Rev.* 72 (1972) 1-42.

Fisher, et al., "Heteroatom-Directed Metalation. Lithiation of N-Propenylbenzamides and N-Propenyl-o -toluamides. Novel Routes to Ortho-Substituted Primary Benzamide Derivatives and N-Unsubstituted Isoquinolin-I(2H)-ones", *J. Org. Chem.* 57 (1992) 2700-2705.

Fukuyama, et al., "2,4-Dinitrobenzenesulfonamides: A Simple and Practical Method for the Preparation of a Variety of Secondary Amines and Diamines", *Tetrahedron Lett.* 38 (1997) 5831-5834.

Greiner, A., "TDA-1 Catalysis in Smiles Rearrangement of N-Arylphenoxyamides. Accelerating Effect of the 2,4,6-Trichloro Substitution," *Tetrahedron Lett.* 30:931-934, 1989.

Guilford, et al., "Synthesis, Characterization, and Structure-Activity Relationships of Amidine-Substituted (Bis)benzylidene-Cycloketone Olefin Isomers as Potent and Selective Factor Xa Inhibitors," *J. Med. Chem.* 42:5415-5425, 1999.

Guo, et al., "Enantioselective Addition of Diethylzinc to Benzaldehyde Catalyzed by Chiral Titanate Complexes with Helical Ligands", *Tetrahedron* 53 (1997) 4145-4158.

Harvey, et al., "o-Nitroaniline Derivatives. Part 11. 4- and 7-Amino-IH-benzimidazole 3-Oxides", *J. Chem. Soc. Perkin Trans.* 1 (1988) 1939-1943.

Insler, V., "Gonadotropin Therapy: New Trends and Insights", *Int. J. Fertil.*, 33 (1988) 85-97.

Jia, et al., "Expression of Human Luteinizing Hormone (LH) Receptor: Interaction with LH and Chorionic Gonadotropin from Human but not Equine, Rat, and Ovine Species", *Mol. Endocrinol.* 5 (1991) 759-768.

Kansai, et al., "Diuretic Agents: Synthesis of 1,2-Disubstituted 7-Sulphamoylbenzimidazole-5-Carboxylic Acids," *Indian J. Chem.* 18B:88-90, 1979.

Katsumi, et al., "Studies on Styrene Derivatives. I. Synthesis and Antiinflammatory Activities of a-Benzylidene-γ-butyrolactone Derivatives", *Chem. Pharm. Bull.* 34 (1986) 121-129.

Kesten, et al., "Synthesis and Antimalarial Properties of 1-Imino Derivatives of 7-Chloro-3-substituted-3,4-dihydro-1,9(2H,10H)-acridinediones and Related Structures", *J. Med. Chem.* 35 (1992) 3429-3447.

Krohn, et al., "Total Synthesis of Angucyclines. Part 15: A Short Synthesis of (±)-6-Deoxybrasiliquinone B", *Tetrahedron* 56 (2000) 4753-4758.

Kuehne, et al., "1,4-Dihydrobenzoic Acid", *Org. Synth. Coll.* 5 (1973) 400.

Kumar, et al., "Synthesis and Evaluation of Anticancer Benzoxazoles and Benzimidazoles Related to UK-1", *Bioorg. & Med. Chem.* 10 (2002) 3997-4004.

Lal, et al., "Regiospecific Oxidation by DDQ of Unhindered Alkyl Groups in Sterically Hindered Aromatic Amines", *Tetrahedron Lett.* 25 (1984) 2901-2904.

Langry, K.C., "Synthesis of Imidazoquinolines and Imidazoisoquinolines From Azanaphthalene Carboxylic Acids", *Org. Prep. Proced. Int.* 26 (1994) 429-438.

Larget, et.al. "A Convenient Extension of the Wessely-Moser Rearrangement for the Synthesis of Substituted Alkylaminoflavones as Neuroprotective Agents In Vitro", *Bioorg. & Med. Chem. Lett.* 10 (2000) 835-838.

Lavilla, R., "Recent developments in the chemistry of dihydropyridines", *J. Chem. Soc., Perkin Trans.* 1 (2002) 1141-1156.

Loev, et al., "Hantzsch-Type Dihydropyridine Hypotensive Agents", *J. Med. Chem.* 17 (1974) 956-965.

Manchand, et al., "Synthesis of 3,4,5-Trimethoxybenzaldehyde", *Synth. Commun.* 20 (1990) 2659-2666.

Mariella, et al., "Synthesis of Some Aromatic Malononitriles", *J. Org. Chem.* 23 (1958) 120-121.

Mayer, et.al., "Über Carbocyclische Reduktone. Dihyrogpyogallol und Dihydrogallussäure", *Chem. Ber.* 88 (1955) 316-327.

McCarthy, et al., "Synthesis and Renal Vasodilator Activity of 2-Chlorodopamine and N-Substituted Derivatives," *J. Med. Chem.* 29: 1586-1590 (1986).

Miri, et al., "Synthesis and Calcium Channel Modulating Effects of Modified Hantzsch Nitrooxyalkyl 1,4-Dihydro-2,6-dimethyl-3-nitro-4-(pyridinyl or 2-trifluoromethylphenyl)-5-pyridinecarboxylates", *Drug Dev. Res.* 51 (2000) 225-232.

Mitchell, et al., "N-Bromosuccinimide-Dimethylformamide: A Mild, Selective Nuclear Monobromination Reagent for Reactive Aromatic Compounds", *J. Org. Chem.* 44 (1979) 4733-4735.

Morse, et al., "Hetrogeneity of Proteins in Commercial Preparations of Human Chorionic Gonadotropin (hCG) Demonstrated by Western Blotting", *Amer. J. Reproduct. Immunol. and Microbiology* 17 (1988) 134-140.

Navot, et al., "The Use of Follicle-Stimulating Hormone for Controlled Ovarian Hyperstimulation in In Vitro Fertilization", *J. In Vitro Fert. Embryo Transf.* 5 (1988) 3-13.

Nguyen, et al., "Hantzsch 1,4-Dihydropyridines Containing a Nitrooxyalkyl Ester Moiety to Study Calcium Channel Antagonist Structure-Activity Relationships and Nitric Oxide Release", *Drug Dev. Res.* 51 (2000) 233-243.

Nobel, D., "The Copper-Carbon Dioxide System, a New Mild and Selective Catalyst for the Methoxylation of Non-activated Aromatic Bromides", *J. Chem. Soc., Chem. Commun.* 4 (1993) 419-420.

Novak, et al, :Hydrolysis and $Fe^{2+}$-Induced Reduction of *N*-Aryl-*O*-pivaloylhydroxylamines: Aqueous Solution Chemistry of Model Carcinogens, *J. Org. Chem.* 53 (1988) 4762-4769.

Olijve, et al., "Molecular Biology and Biochemistry of Human Recombinant Follicle Stimulating Hormone (Puregon®)", *Mol. Hum. Reprod.* 2 (1996) 371-382.

Olson, et al., "A Dopamine Receptor Model and its Application in the Design of a New Class of Rigid Pyrrolo[2,3-g]isoquinoline Antipsychotics", *J. Med. Chem.* 24 (1981) 1026-1034.

Raviñe, et al., "Conformationally Constrained Butyrophenones with Affinity for Dopamine (D1, D2, D4) and Serotonin (5-HT2A, 5-HT2B, 5-HT2C) Receptors: Synthesis of Aminomethylbenzo[b]furanones and Their Evaluation as Antipsychotics", *J. Med. Chem.* 43 (2000) 4678-4693.

Sainani, et al., "Synthesis of 4-aryl-1,4,5,6,7,8-hexahydro-5-oxo-2,7,7-trimethylquinoline-3-carboxylates and amides", *Indian J. Chem.* 33B (1994) 526-531.

Sarma, et al., "Solid State Nuclear Bromination with N-Bromosuccinimide. Part 2. Experimental and theoretical studies of reactions with some substituted benzaldehydes", *J. Chem. Soc., Perkin Trans.* 2, (2000) 1119-1124.

Sarma, et al., "Solid State Nuclear Bromination with N-bromosuccinimide. Part 1. Experimental and theoretical studies on some substituted aniline, phenol and nitro aromatic compounds", *J. Chem. Soc., Perkin Trans.* 2, (2000) 1113-1118.

Shadyro et al, "Synthesis and Antiviral Activity of N-Acyl Derivatives of 4,6-Di-(*tert*-Butyl)-2-Aminophenol", *Pharm. Chem. J.*, 36 (2002) 410-412.

Sharma, et al., "Syntheses of Some Mannich Bases of Formyl & Other Substituted Phenols as Potential Spermicides", *Indian J. Chem.*, 20B (1981) 1010-1013.

Sharpe, R.M., "Intratesticular Control of Steroidogenesis", *Clin. Endocrinol.*, 33 (1990) 787-807.

Shilcrat, et al., "A New Regioselective Synthesis of 1,2,5-Trisubstituted 1H-Imidazoles and its Application to the Development of Eprosartan ," *J. Org. Chem.* 62:8449-8454, 1997.

Sircar, et al., "Calcium Channel Blocking and Positive Inotropic Activities of Ethyl 5-Cyano-1,4-dihydro-6-methyl-2-[(phenylsulfonyl)methyl]-4-aryl-3-pyridine-carboxylate and Analogues. Synthesis and Structure-Activity Relationships", *J. Med. Chem.*, 34 (1991) 2248-2260.

Stratowa, et al., "Use of a luciferase reporter system for characterizing G-protein-linked receptors", *Curr. Opin. Biotechnol.*, 6 (1995) 574-581.

Theilacker, et al.,"Zur Konstitution dér Triacylmethane. II. Über das Bicyclo-[2,2,2]-octantrion-(2,6,7)", *Justus Liebig's Annalen der Chemie*, 570 (1950) 15-33.

Turconi, et al., "Synthesis of a New Class of 2,3-Dihydro-2-oxo-1H-benzimidazole-1-carboxylic Acid Derivatives as Highly Potent 5-HT3 Receptor Antagonists", *J. Med. Chem.*, 33 (1990) 2101-2108.

Vierhapper, et al., "Zur Sauerstoffoxidation von Kreosolderivaten in alkalisch-wäβriger Lösung", *Monatsh. Chem.*, 106 (1975) 1191-1201.

Visentin, et al. "Synthesis and Voltage-Clamp Studies of Methyl 1,4-Dihydro-2,6-dimethyl-5-nitro-4-(benzofurazanyl)pyridine-3-carboxylate Racemates and Enantiomers and of Their Benzofuroxanyl Analogues," *J. Med. Chem.*, 42 (1999) 1422-1427.

Vitolina, et al. "Synthesis and Study of the pharmacological activity of derivatives of condensed 1, 4-dihydropyridines," *Khimiko-Farmatsevticheskii Zhurnal*, 15 (1981) 39-42.

Wadia, et al., "A Convenient Preparation of N-Alkyl and N-Arylamines by Smiles Rearrangement-Synthesis of Analogues of Diclofenac," *Synth. Commun.*, 33:2725-2736, 2003.

White, et al., "Resistance-Modifying Agents. 9. Synthesis and Biological Properties of Benzimidazole Inhibitors of the DNA Repair Enzyme Poly(ADP-ribose) Polymerase", *J. Med. Chem.*, 43 (2000) 4084-4097.

Wong, et al., "Identification of a Dihydropyridine as a Potent α1a Adrenoceptor-Selective Antagonist That Inhibits Phenylephrine-Induced Contraction of the Human Prostate", *J. Med. Chem.*, 41 (1998) 2643-2650.

Yagupolskii, et al., "Vasorelaxation by New Hybrid Compounds Containing Dihydropyridine and Pinacidil-Like Moieties", *J. Med. Chem.*, 42 (1999) 5266-5271.

Database CAPLUS Chemical Abstracts Service, Columbus, Ohio, US; XP-002288485 retrieved from STN accession No. 1802 Database accession No. 1981:497547.

XP-002369583 Retrieved from STN, Database Registry [Online] RN:330674-72-1, Apr. 10, 2001.

Search Report issued on May 12, 2005 in connection with PCT Intl. Appln. No. PCT/EP2005/052042.

Written Opinion issued on Nov. 4, 2007 in connection with PCT Intl. Appln. No. PCT/EP2005/052042.

International Preliminary Report on Patentability issued on Nov. 6, 2007 in connection with PCT Intl. Appln. No. PCT/EP2005/052042.

Search Report issued on Aug. 18, 2006 in connection with PCT Intl. Appln. No. PCT/EP2006/061972.

Written Opinion issued on Nov. 4, 2007 in connection with PCT Intl. Appln. No. PCT/EP2006/061972.

International Preliminary Report on Patentability issued on Nov. 6, 2007 in connection with PCT Intl. Appln. No. PCT/EP2006/061972.

Search Report issued on Jul. 5, 2006 in connection with PCT Intl. Appln. No. PCT/EP2006/061976.

Written Opinion issued on Nov. 4, 2007 in connection with PCT Intl. Appln. No. PCT/EP2006/061976.

International Preliminary Report on Patentability issued on Nov. 6, 2007 in connection with PCT Intl. Appln. No. PCT/EP2006/061976.

Search Report issued on Jul. 5, 2006 in connection with PCT Intl. Appln. No. PCT/EP2006/061978.

Written Opinion issued on Nov. 4, 2007 in connection with PCT Intl. Appln. No. PCT/EP2006/061978.

International Preliminary Report on Patentability issued on Nov. 6, 2007 in connection with PCT Intl. Appln. No. PCT/EP2006/061978.

Non-Final Rejection issued Jan. 8, 2010 in connection with US2009/0215773.

* cited by examiner

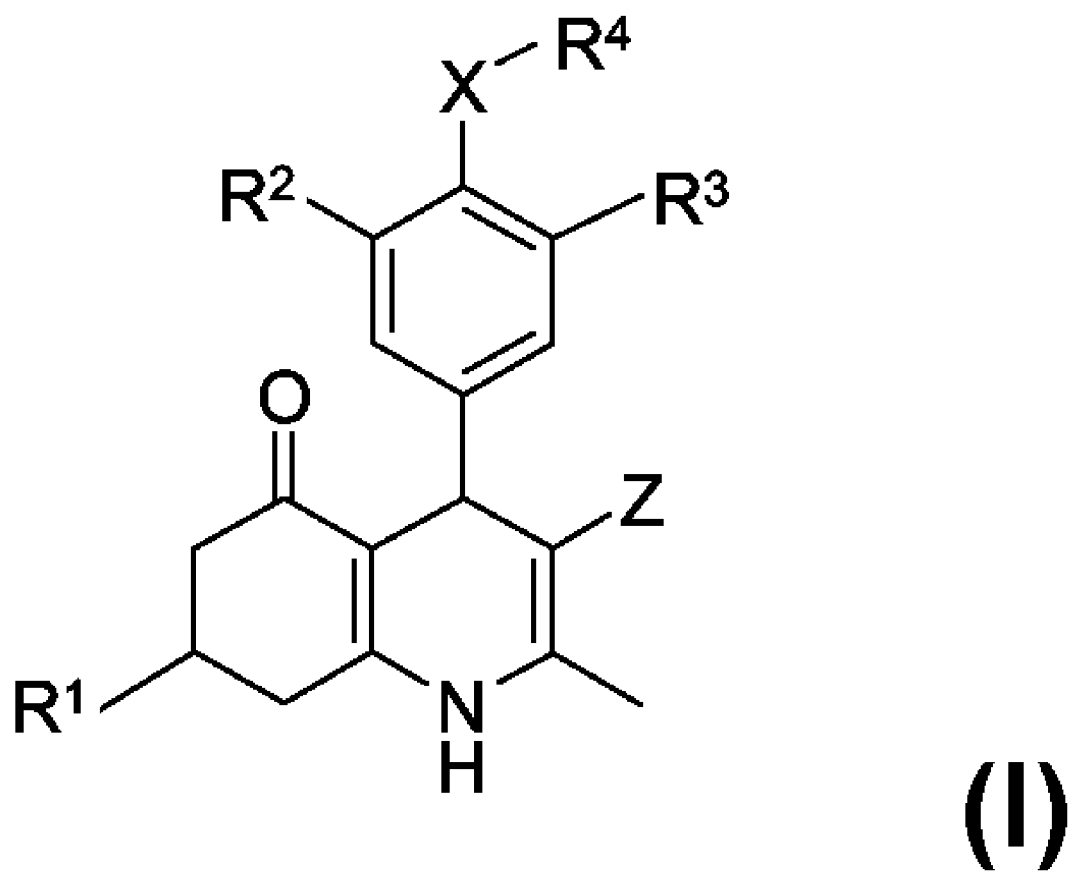
(I)

4-PHENYL-5-OXO-1,4,5,6,7,8-HEXAHYDRO QUINOLINE DERIVATIVES AS MEDICAMENTS FOR THE TREATMENT OF INFERTILITY

CROSS REFERENCE TO RELATED APPLICATION

This application claims priority based on International Patent Application No. PCT/EP2006/061978, filed on May 2, 2006.

FIELD OF THE INVENTION

The present invention relates to 2-methyl-4-phenyl-5-oxo-1,4,5,6,7,8-hexahydroquinoline derivatives, to pharmaceutical compositions comprising the same and to the use of said derivatives for the manufacture of medicaments for the treatment of infertility.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm. Res. 35:301-342, 1979). Currently, FSH is applied clinically for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992). The actions of the FSH hormone are mediated by a specific plasma membrane receptor that is a member of the large family of G-protein coupled receptors. These receptors consist of a single polypeptide with seven transmembrane domains and are able to interact with the Gs protein, leading to the activation of adenylate cyclase.

The FSH receptor is a highly specific target in the ovarian follicle growth process and is exclusively expressed in the ovary. Blocking of the receptor or inhibiting the signalling which is normally induced after FSH-mediated receptor activation will disturb follicle development and thus ovulation and fertility. Low molecular weight FSH antagonists could form the basis for new contraceptives, while low molecular weight FSH agonists can be used for the same clinical purposes as native FSH, i.e. for the treatment of infertility and for ovarian hyperstimulation on behalf of in vitro fertilisation.

Low molecular weight FSH mimetics with agonistic properties were disclosed in the International Application WO 2000/08015 (Applied Research Systems ARS Holding N.V.) and in WO 2002/09706 (Affymax Research Institute).

Certain tetrahydroquinoline derivatives have recently been disclosed in the International Application WO 2003/004028 (AKZO NOBEL N.V.) as FSH modulating substances, either having agonistic or antagonistic properties.

There remains a need for low molecular weight hormone mimetics that selectively activate the FSH receptor.

To that aim the present invention provides 2-methyl-4-phenyl-5-oxo-1,4,5,6,7,8-hexahydroquinoline derivatives of general formula I

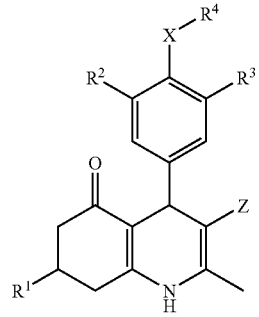

Formula I wherein
$R^1$ is (1-6C)alkyl, (2-6C)alkenyl or (2-6C)alkynyl;
$R^2$ is halogen;
$R^3$ is $SO_2NR^5R^6$ or (1-4C)alkoxy, optionally substituted with one of more fluorine atoms;
X is O or $NR^7$;
$R^4$ is $R^8$-(2-8C)alkyl, $R^8$-(3-8C)alkenyl, $R^8$-(3-8C)alkynyl or $R^8$-(2-4C)alkoxy(2-4C)-alkyl;
Z is CN or $NO_2$;
$R^5$ and $R^6$ are independently H or (1-4C)alkyl; or
$R^5$ together with $R^6$ and the N to which they are bonded form a 3-8 membered saturated ring optionally containing a further heteroatom selected from O and S;
$R^8$ is OH, (1-4C)alkoxy, $NH_2$; $NR^9C(O)R^{11}$, $NR^9SO_2R^{11}$ or $C(O)NR^9R^{10}$;
$R^7$ and $R^9$ are independently H or (1-4C)alkyl;
$R^{10}$ is (1-4C)alkyl, (1-4C)alkoxy(1-4C)alkyl, or phenyl(1-4C)alkyl or
(2-5C)heteroaryl(1-4C)alkyl, both optionally substituted on the (hetero)aromatic ring with one or more substituents selected from OH, $NH_2$, halogen, $NO_2$, $CF_3$, CN, (1-4C)-alkyl, (1-4C)alkoxy and (di)(1-4C)alkylamino;
$R^{11}$ is (1-4C)alkyl, (2-4C)alkenyl, (2-4C)alkynyl, (1-4C) alkoxy(1-4C)alkyl, (3-6C)-cycloalkyl, (1-4C)alkoxy, (di)(1-4C)alkylamino, or phenyl or (2-5C)heteroaryl, both optionally substituted on the (hetero)aromatic ring with one or more substituents selected from OH, $NH_2$, halogen, $NO_2$, $CF_3$, CN, (1-4C)alkyl, (1-4C)alkoxy and (di)(1-4C)alkylamino; or a pharmaceutically acceptable salt thereof.

DETAILED DESCRIPTION OF THE INVENTION

The 2-methyl-4-phenyl-5-oxo-1,4,5,6,7,8-hexahydroquinoline derivatives according to the present invention are potent FSH receptor activators and can be used for the same clinical purposes as native FSH since they behave like agonists, with the advantage that they may be prepared synthetically, may display altered stability properties and may be administered differently.

Thus, the FSH-receptor agonists of the present invention may be used for the treatment of fertility disorders e.g. controlled ovarian hyperstimulation and IVF procedures.

The term (1-4C)alkyl as used in the definition means a branched or unbranched alkyl group having 1-4 carbon atoms, being methyl, ethyl, propyl, isopropyl, butyl, sec-butyl and tert-butyl.

The term (1-6C)alkyl means a branched or unbranched alkyl group having 1-6 carbon atoms, for example methyl, ethyl, propyl, isopropyl, butyl, isobutyl, tert-butyl, n-pentyl and n-hexyl.

The term (2-4C)alkyl as used in the definition means a branched or unbranched alkyl group having 2-4 carbon atoms.

The term (2-8C)alkyl as used in the definition means a branched or unbranched alkyl group having 2-8 carbon atoms.

The term (3-8C)alkenyl means a branched or unbranched alkenyl group having 3-8 carbon atoms, such as 2-propenyl, 2-butenyl, 3-butenyl, pentenyl, hexenyl and octenyl.

The term (2-6C)alkenyl means a branched or unbranched alkenyl group having 2-6 carbon atoms, such as ethenyl, n-propenyl, 2-methyl-2-propenyl, 2-butenyl, 3-butenyl, pentenyl and hexenyl.

The term (2-4C)alkenyl likewise means a branched or unbranched alkenyl group having 2-4 carbon atoms, such as ethenyl, 2-propenyl, 2-methyl-2-propenyl, 2-butenyl and 3-butenyl.

The term (3-8C)alkynyl means a branched or unbranched alkynyl group having 3-8 carbon atoms, such as 2-propynyl, 2-butynyl, 3-butynyl, pentynyl, hexynyl and octynyl.

The term (2-6C)alkynyl means an alkynyl group having 2-6 carbon atoms, such as ethynyl, 2-propynyl, 2-butynyl, 3-butynyl, pentynyl and hexynyl.

The term (2-4C)alkynyl likewise means an alkynyl group having 2-4 carbon atoms, such as ethynyl, 2-propynyl, 2-butynyl and 3-butynyl.

The term (1-4C)alkoxy means an alkoxy group having 1-4 carbon atoms, the alkyl moiety having the same meaning as previously defined. (1-2C)Alkoxy groups are preferred.

The term (3-6C)cycloalkyl means a cycloalkyl group having 3-6 carbon atoms, being cyclopropyl, cyclobutyl, cyclopentyl and cyclohexyl.

The term (3-6C)cycloalkyl(1-4C)alkyl means a cycloalkylalkyl group, the cycloalkyl group of which has 3-6 carbon atoms with the same meaning as previously defined and the alkyl group having 1-4 carbon atoms with the same meaning as previously defined.

The term (2-5C)heteroaryl means a substituted or unsubstituted aromatic group having 2-5 carbon atoms and at least including one heteroatom selected from N, O and S, like imidazolyl, thiadiazolyl, pyridinyl, thienyl or furyl. Preferred heteroaryl groups are thienyl, furyl and pyridinyl. The (2-5C)heteroaryl group may be attached via a carbon atom or a heteroatom, if feasible.

The term (2-5C)heteroaryl(1-4C)alkyl means a heteroarylalkyl group, the heteroaryl group of which contains 2-5 carbon atoms with the same meaning and preferences as previously defined and the alkyl group contains 1-4 carbon atoms with the same meaning as previously defined. The (2-5C)heteroaryl group may be substituted on the (hetero)aromatic ring with one or more substituents selected from OH, $NH_2$, halogen, $NO_2$, $CF_3$, CN, (1-4C)alkyl, (1-4C)alkoxy and (di)(1-4C)alkylamino.

The term phenyl(1-4C)alkyl means a phenyl group attached to an alkyl group having 1-4 carbon atoms as defined previously. The phenyl group may be substituted with one or more substituents selected from OH, $NH_2$, halogen, $NO_2$, $CF_3$, CN, (1-4C)alkyl, (1-4C)alkoxy and (di)(1-4C)alkylamino.

The term (di)(1-4C)alkylamino as used herein means an amino group, monosubstituted or disubstituted with alkyl groups, each of which contains 1-4 carbon atoms and has the same meaning as previously defined.

In the definition of Formula I $R_5$ together with $R_6$ and the N to which they are bonded may form a 3-8 membered ring, optionally containing a further heteroatom selected from O and S. Examples of such ring are pyrrolidin-1-yl, piperidin-1-yl, azepin-1-yl, morpholin-4-yl and thiomorpholin-4-yl.

The term halogen means fluorine, chlorine, bromine or iodine; chlorine, bromine or iodine being preferred.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like.

In one aspect the invention concerns compounds according to formula I wherein X=O.

The invention also relates to compounds of formula I, wherein $R^1$ is (1-6C)alkyl. In particular, the invention relates to compounds wherein $R^1$ is (1-4C)alkyl. Most particularly, $R^1$ is n-propyl.

Another aspect of the invention are compounds according to formula I wherein $R^2$ is Cl, Br or I.

In yet another aspect, the invention concerns compounds of formula I, wherein Z is CN.

The invention also relates to compounds according to general Formula I wherein $R^3$ is $SO_2NR^5R^6$.

Still another aspect of the invention concerns compounds wherein one or more of the specific definitions of the groups $R^1$ through $R^{11}$ and X and Z as defined here above are combined in the definition of the 2-methyl-4-phenyl-5-oxo-1,4,5,6,7,8-hexahydroquinoline derivatives of formula I.

Yet another aspect of the invention concerns compounds according to Formula I which have an $EC_{50}$ in the binding assay of less than $10^{-8}$ M (as described in example 33).

Suitable methods for the preparation of the 2-methyl-4-phenyl-5-oxo-1,4,5,6,7,8-hexahydroquinoline derivatives of the invention are outlined below.

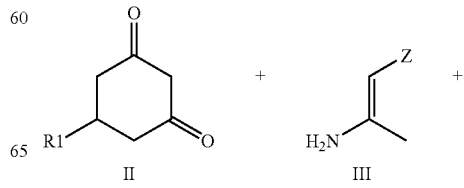

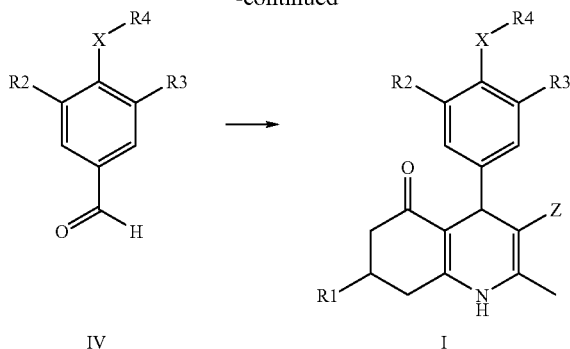

The 1,4,5,6,7,8-hexahydroquinoline derivatives I of the present invention can be prepared starting from cyclohexane-1,3-diones of general formula II, enamines of general formula III and benzaldehydes of general formula IV, wherein $R^1$, $R^2$, $R^3$, $R^4$, X and Z are as previously defined, by the well-documented three component Hantzsch-type cyclo-condensation reaction.

Related Hantzsch-type cyclo-condensation reactions can be found in: Bioorg. Med. Chem. Lett. 12 (2002) 1481-1484, J. Chem. Soc., Perkin Trans. 1 (2002) 1141-1156, Synlett (2002) 89-92, Drug Dev. Res. 51 (2000) 233-243, J. Med. Chem. 42 (1999) 1422-1427, ibid. 5266-5271, ibid. 41 (1998) 2643-2650, WO 9408966, Arzneim.-Forsch./Drug Res. 45 (1995) 1054-1056, J. Med. Chem. 34 (1991) 2248-2260, ibid. 17 (1974) 956-65, Chem. Rev. 72 (1972), 1-42. The above mentioned reaction is typically conducted at elevated temperature in a protic solvent like for example acetic acid, (iso)propanol, ethanol, methanol or mixtures thereof.

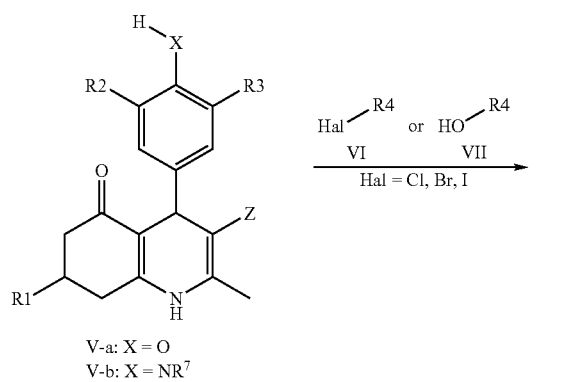

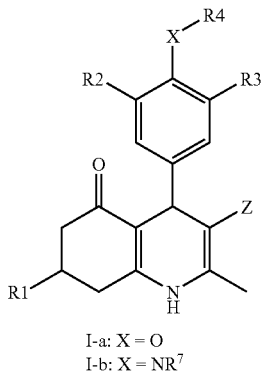

Alternatively, compounds of general formula I-a, wherein $R^1$, $R^2$, $R^3$, $R^4$ and Z are as previously defined and X=O, can be obtained by standard O-alkylation of compounds of general formula V-a. In a typical experiment, compounds V-a are reacted in a solvent, such as dichloromethane, N,N-dimethylformamide, dimethyl sulfoxide, ethanol, tetrahydrofuran, 1,4-dioxane or toluene with appropriately substituted alkyl halides of formula VI (Hal=Cl, Br, I), in the presence of a base such as triethylamine, N,N-diisopropylethylamine (DiPEA), potassium carbonate, cesium carbonate or sodium hydride, optionally in the presence of a catalytic amount of potassium iodide or tetrabutylammonium iodide, to give O-alkylated derivatives of formula I-a. Alternatively, O-alkylated compounds of general formula I-a can be obtained by using art known Mitsunobu reactions with alcohols of formula VII, triphenylphosphine (optionally resin bound) and a dialkyl azodicarboxylate (e.g. diethyl azodicarboxylate) in appropriate solvents such as 1,4-dioxane, tetrahydrofuran or dichloromethane at elevated or ambient temperature.

Likewise, compounds of general formula I-b, wherein $R^1$, $R^2$, $R^3$, $R^4$ and Z are as previously defined and X=$NR^7$, can be obtained by N-alkylation of compounds of general formula V-b with compounds of general formula VI, using the same methods as described for the conversion of compounds V-a to I-a.

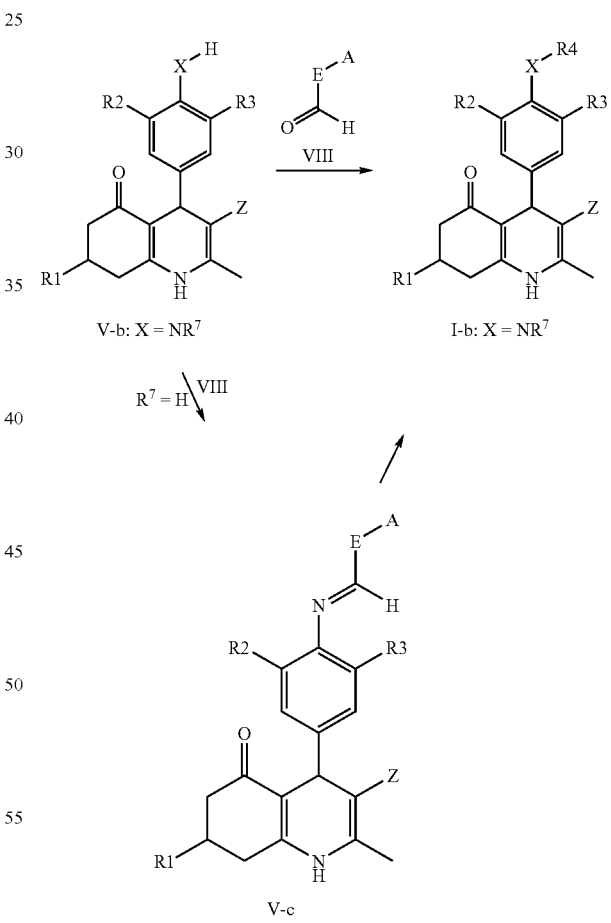

Alternatively, compounds of general formula I-b can be prepared by reductive amination of appropriately substituted aldehydes of formula VIII, wherein E-A is a substituted alkyl group (e.g. 3-ethoxy-propionaldehyde, (2-methoxy-ethoxy)-acetaldehyde, 7-hydroxy-pentanal) with compounds V-b and a suitable reducing agent such as sodium cyanoborohydride or sodium triacetoxyborohydride, or zinc/acetic acid. Reductive amination reactions are well known in the art. Additionally, compounds of general formula V-b can be converted to the corresponding imines of formula V-c upon reaction with aldehydes VIII by methods well known to those skilled in the art, followed by reduction with a reducing agent such as sodium borohydride to give compounds I-b.

azido, cyano, carboxylic acid, ester and the like) which can be eventually be converted to groups defined for $R^8$.

For example, compounds of general formula I-c can be obtained by removal of a protective group from compounds of general formula IX-a, wherein PG is a suitable

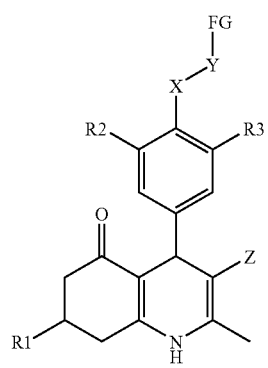

IX: Y = alkyl, alkenyl, alkynyl or alkoxyalkyl group
FG = functional group

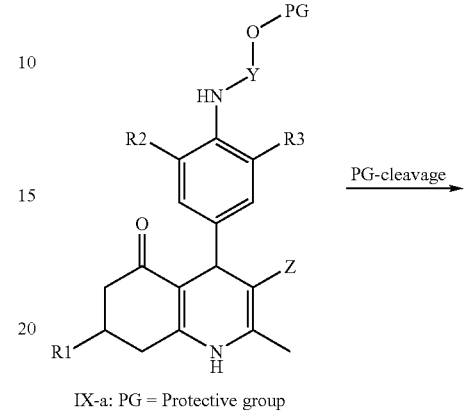

IX-a: PG = Protective group

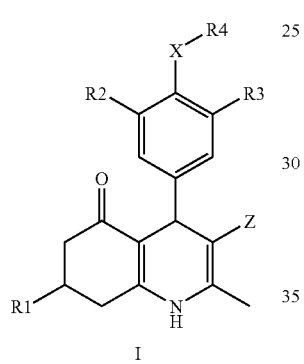

I

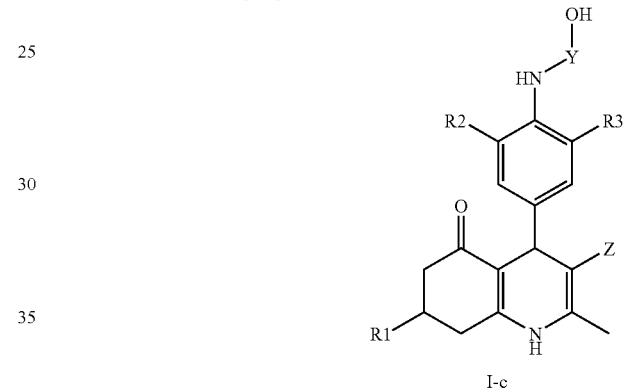

I-c

Y is an alkyl, alkenyl, alkynyl or alkoxyalkyl group

Additionally, the 1,4,5,6,7,8-hexahydroquinoline derivatives I of the present invention can be prepared starting from appropriately functionalised 1,4,5,6,7,8-hexahydroquinoline derivatives of general structure IX, wherein $R^1$, $R^2$, $R^3$, X and Z are as previously defined and Y is a substituted alkyl, alkenyl, alkynyl or alkoxyalkyl group and FG is a functional group (e.g. halide, protected hydroxyl, protected amino, protective group, such as t-butyldimethylsilyl (TBDMS), tetrahydropyranyl (THP) or benzoate. Protective group manipulations are well known in the art: For example, see: *Protective groups in Organic Synthesis*, T. W. Greene and P. G. M. Wuts, John Wiley & sons, Inc., New York, 1999.

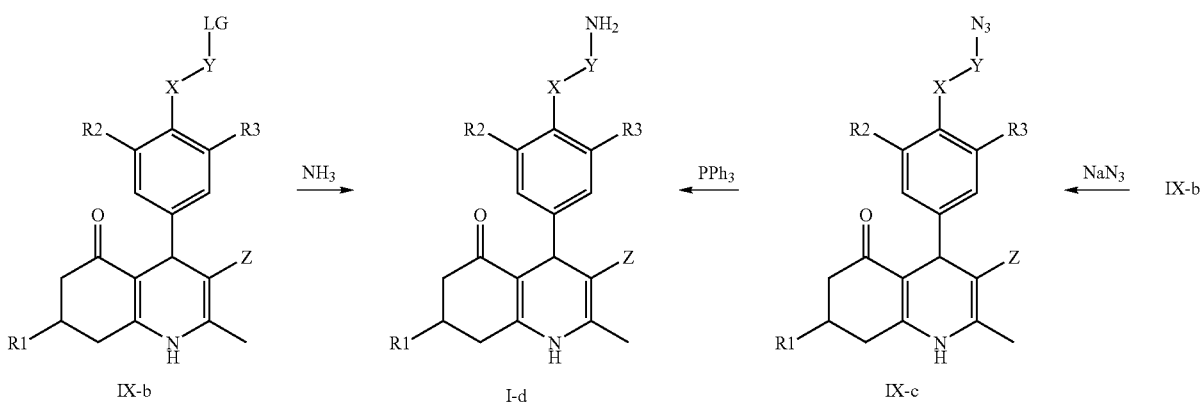

IX-b
LG = OMs, OTs, Br, Cl

I-d

IX-c

Y is an alkyl, alkenyl, alkynyl or alkoxyalkyl group

Compounds of general formula I-d, wherein $R^1$, $R^2$, $R^3$, X and Z are as previously defined, are prepared from compounds of general formula IX-b in which LG is a leaving group by treatment with aqueous ammonia in a suitable solvent such as 1,4-dioxane, acetonitrile or tetrahydrofuran. Alternatively, compounds of general formula IX-b can be treated with sodium azide in a suitable solvent such as N,N-dimethylformamide or tetrahydrofuran, to yield compounds of general formula IX-c, which can be reduced by the art-known Staudinger reduction using triphenylphosphine (optionally resin bound) in wet THF, optionally in the presence of aqueous HCl to give compounds of general formula I-d.

In the specific cases of compounds IX-d wherein LG is bromide in an allylic position, the reaction with sodium azide followed by Staudinger reduction can afford

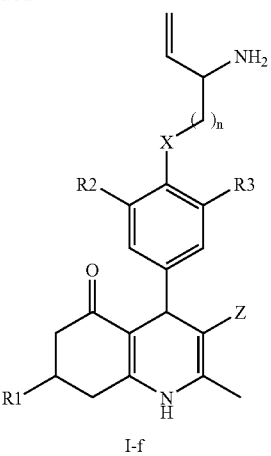

n = 1, 2, 3, 4, 5 regioisomeric products, being compounds of general formulas I-e and I-f, respectively.

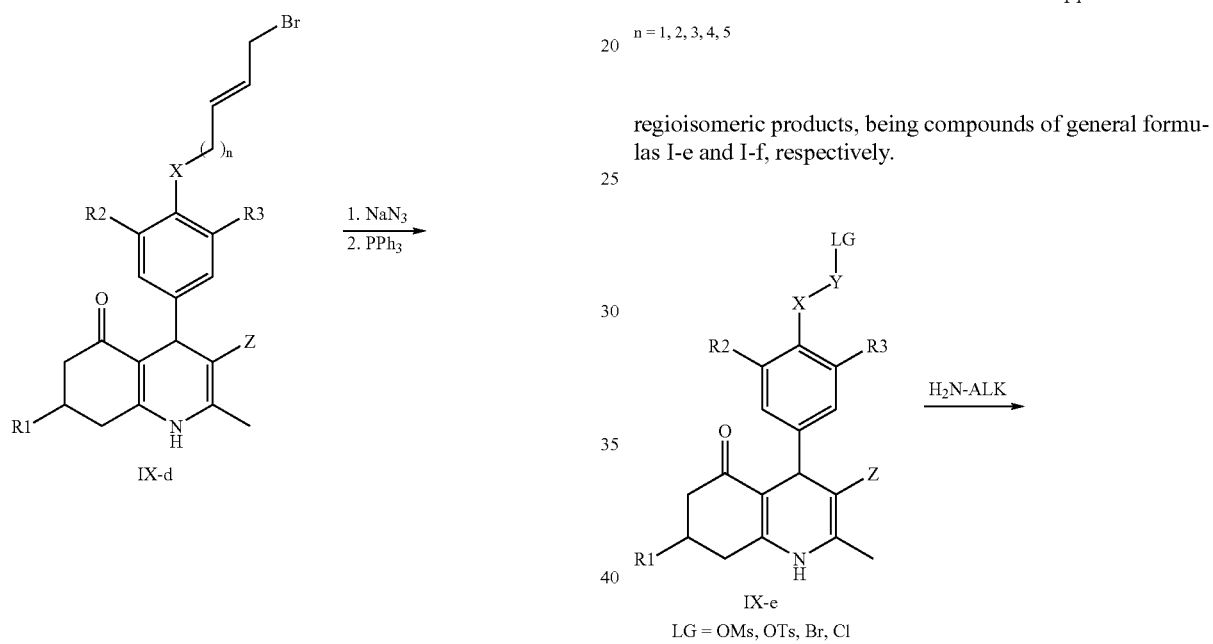

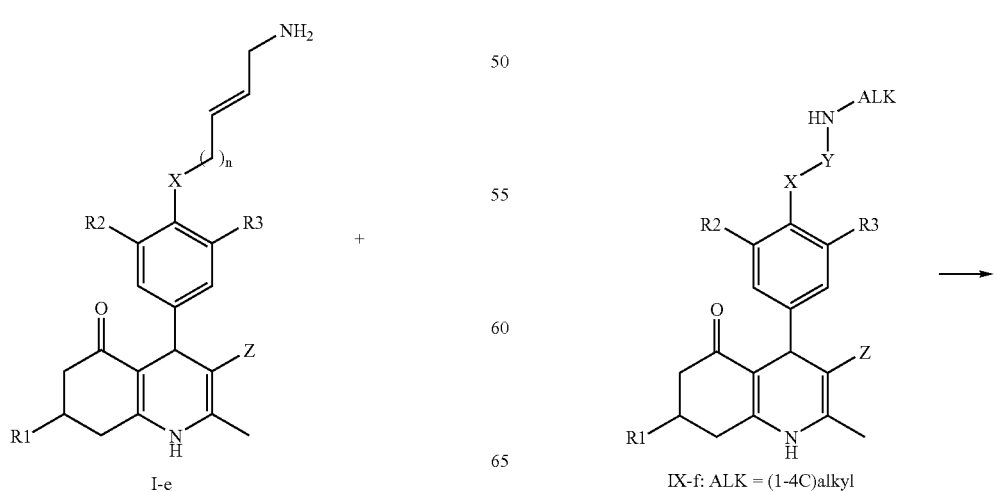

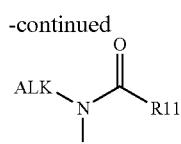

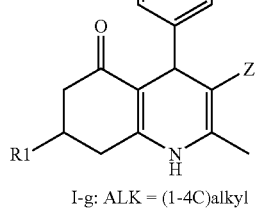

I-g: ALK = (1-4C)alkyl

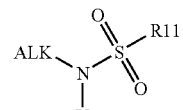

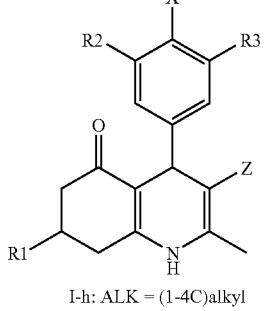

I-h: ALK = (1-4C)alkyl

Y is an alkyl, alkenyl, alkynyl or alkoxyalkyl group

Compounds of general formula I-g and I-h, wherein $R^1$, $R^2$, $R^3$, $R^{11}$, X and Z are as previously defined, can be prepared by standard N-acylation or N-sulfonylation of compounds of general formula IX-f, which are synthesized from derivatives IX-e and (1-4C)alkylamines of general formula $H_2N$-Alk. In a typical experiment, compounds IX-f are reacted in a solvent, such as dichloromethane, N,N-dimethylformamide, ethanol, tetrahydrofuran, 1,4-dioxane, toluene, 1-methyl-pyrrolidin-2-one or pyridine with an appropriately substituted acyl halide (e.g. $R^{11}$—C(O)—Cl), acid anhydride ($R^{11}$—C(O)—O—C(O)—$R^{11}$) or sulfonyl halide (e.g. $R^{11}$—$SO_2$—Cl) in the presence of a base such as triethylamine, N,N-diisopropylethylamine (DiPEA) or pyridine, to give N-acylated or N-sulfonylated derivatives of formula I-g and I-h, respectively. Alternatively, N-acylated compounds of general formula I-g can be obtained by reaction of derivatives IX-f with a carboxylic acids of general formula $R^{11}$—COOH in the presence of a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU) and a tertiary amine base (e.g. DiPEA) in a solvent such as N,N-dimethylformamide or dichloromethane at ambient or elevated temperature.

Carboxylic acid derivatives of general formula IX-h, accessible by saponification of corresponding alkyl esters IX-g, can be condensed with amines of general structure $R^9R^{10}$NH using a coupling reagent—as described previously for the preparation of derivatives I-g from compounds IX-f—to give compounds of formula I-i, wherein $R^1$, $R^2$, $R^3$, $R^9$, $R^{10}$, X and Z are as previously defined and Y is an alkyl, alkenyl, alkynyl or alkoxyalkyl group. Alternatively, compounds of general formula IX-h can be converted to the corresponding acid chlorides IX-i by art known methods: Treatment of carboxylic acids of general formula IX-h with thionyl chloride or oxalyl chloride and DMF in a suitable solvent such as dichloromethane or toluene gives the corresponding acid chlorides IX-i. Subsequent reaction with amines of general structure $R^9R^{10}$NH, optionally in the presence of a suitable tertiary amine base, yields compounds of general formula I-i.

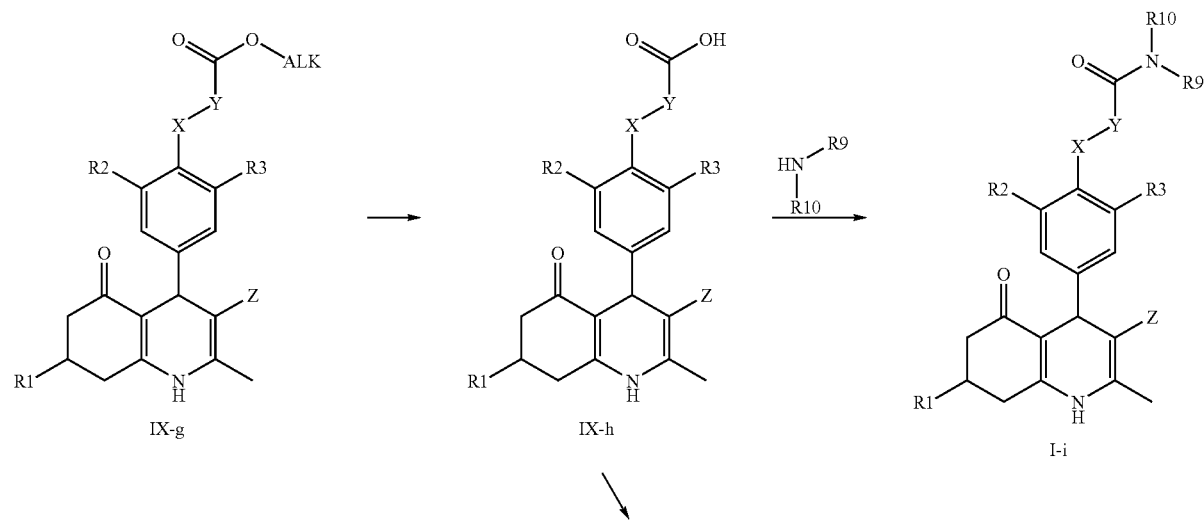

-continued

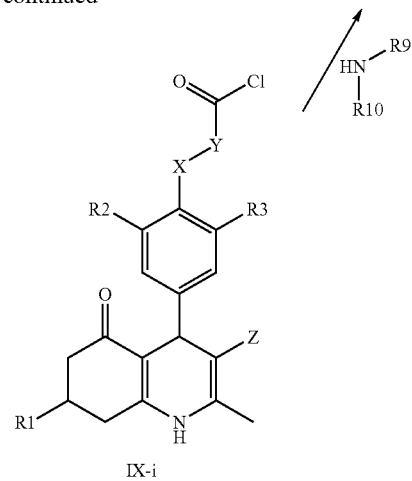

Y is an alkyl, alkenyl, alkynyl or alkoxyalkyl group

Compounds of general formula I-d can be N-acylated to give compounds of general

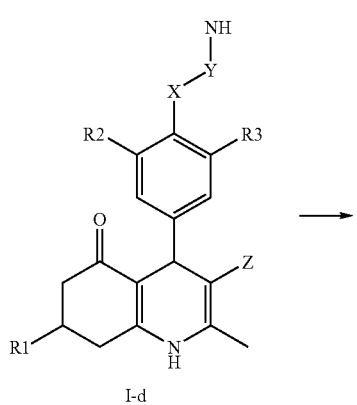

-continued

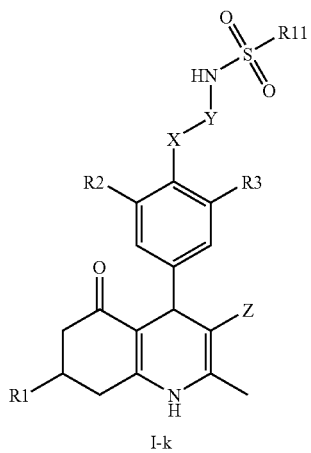

Y is an alkyl, alkenyl, alkynyl or alkoxyalkyl group formula I-j, wherein $R^1$, $R^2$, $R^3$, $R^{11}$, X and Z are as previously defined. These acylations can be achieved using the same synthetic procedures that were described for the preparation of derivatives I-g from compounds IX-f.

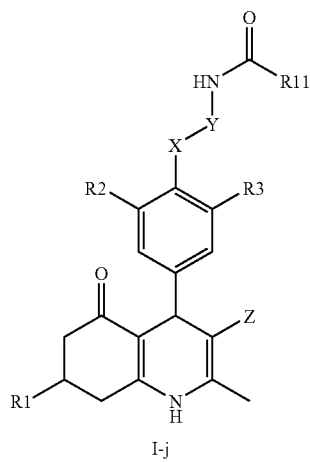

Similar to the N-sulfonylation reactions of derivatives IX-f to give compounds I-h, compounds I-d can be sulfonylated to give compounds I-k, wherein $R^1$, $R^2$, $R^3$, $R^{11}$, X and Z are as previously defined.

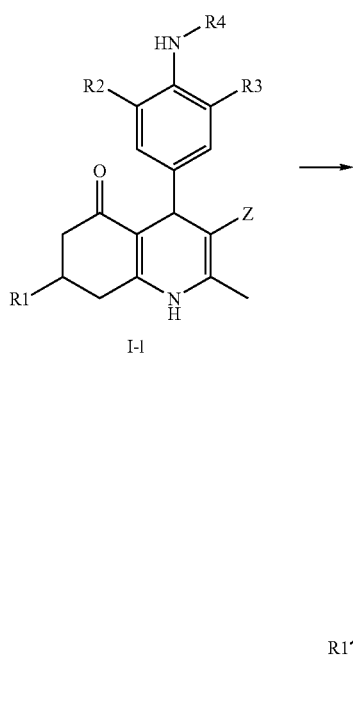

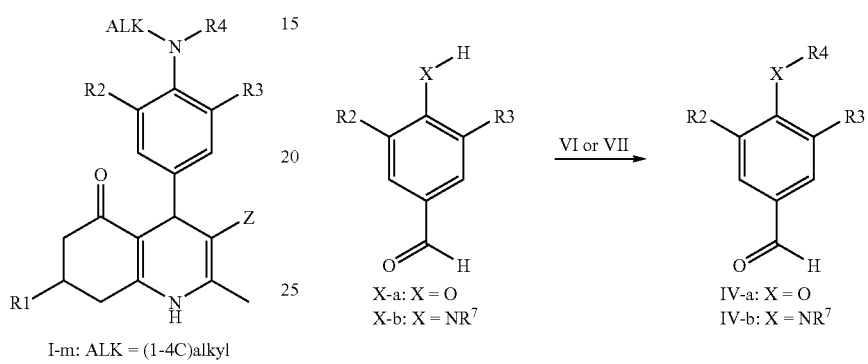

Compounds of general formula I-1, wherein $R^1$, $R^2$, $R^3$, $R^4$ and Z are as previously defined, can be reductively alkylated with simple aldehydes or ketones (formaldehyde, acetaldehyde, propionaldehyde, butyraldehyde, acetone or butan-2-one), using the same methodology as described for the preparation of compounds I-b from V-b, to give compounds of general formula I-m, wherein $R^1$, $R^2$, $R^3$, $R^4$ and Z are as previously defined.

The substituted cyclohexane-1,3-diones of general formula II are commercially available or can be prepared by literature procedures. Relevant examples are found in: J. Med. Chem. 43 (2000) 4678-4693, Tetrahedron 56 (2000) 4753-4758, J. Med. Chem. 35 (1992) 3429-3447, ibid. 24 (1981) 1026-1034, Org. Synt. Coll. Vol. V (1973) 400, Chem. Ber. 88 (1955) 316-327, Justus Liebig Ann. Chem. 570 (1950) 15-31.

The compound of formula III-a is commercially available and compound II-b has been documented in literature, see for example: Drug Dev. Res. 51 (2000) 225-232.

Benzaldehydes of general formula IV-a, wherein $R^2$, $R^3$ and $R^4$ are as previously defined and X=O, are readily prepared from benzaldehydes of general formula X-a using the same methods as described for the conversion of compounds of formula V-a to 1-a. Likewise, compounds of general formula IV-b, wherein $R^2$, $R^3$ and $R^4$ are as previously defined and X=N—$R^7$, are prepared from derivatives X-b using the same methods as described for the conversion of compounds of formula V-b to derivatives I-b.

The 1,4,5,6,7,8-hexahydroquinoline derivatives of general formula V can be prepared by the aforementioned Hantzsch-type cyclocondensation reaction between cyclohexanediones II, enamines III and aldehydes X.

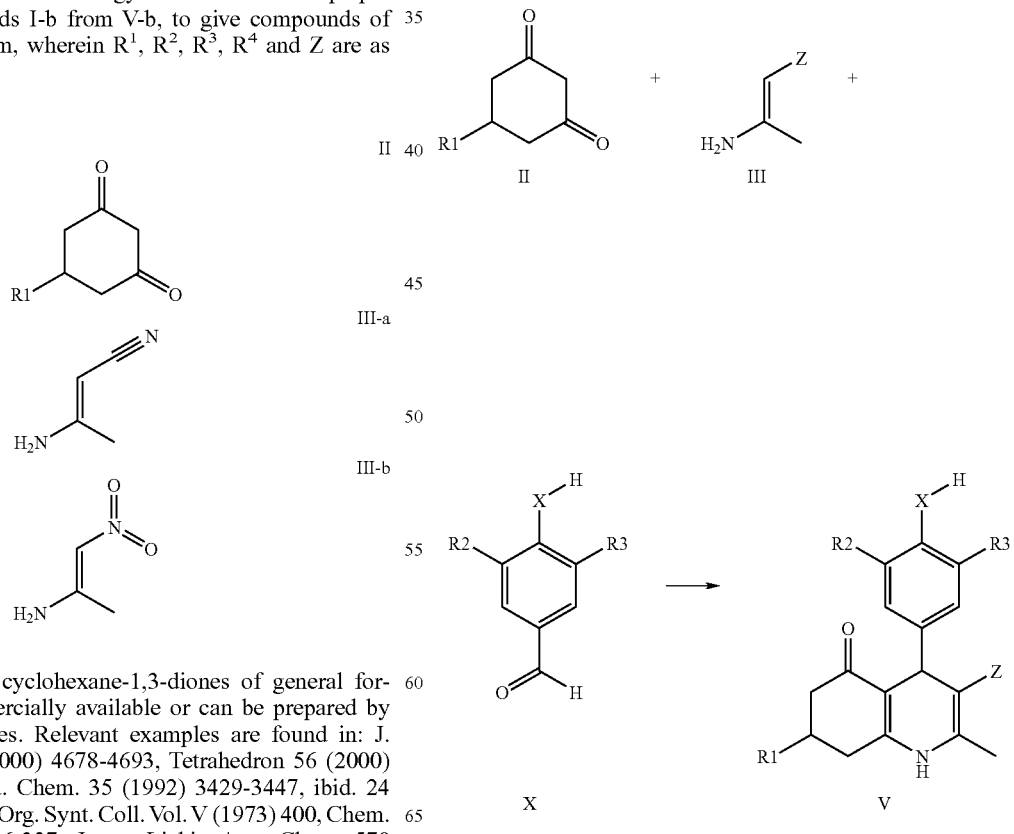

Compounds of general formula V-d-e in which R² is Br can also be obtained by ortho-bromination

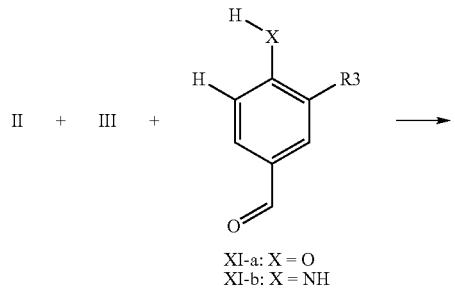

XI-a: X = O
XI-b: X = NH

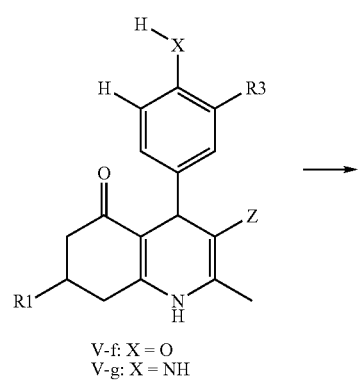

V-f: X = O
V-g: X = NH

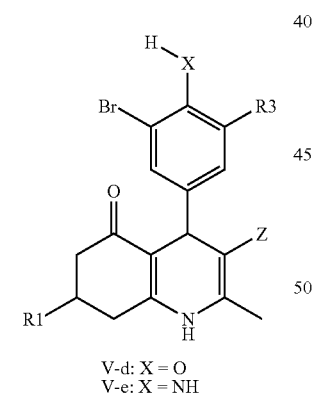

V-d: X = O
V-e: X = NH

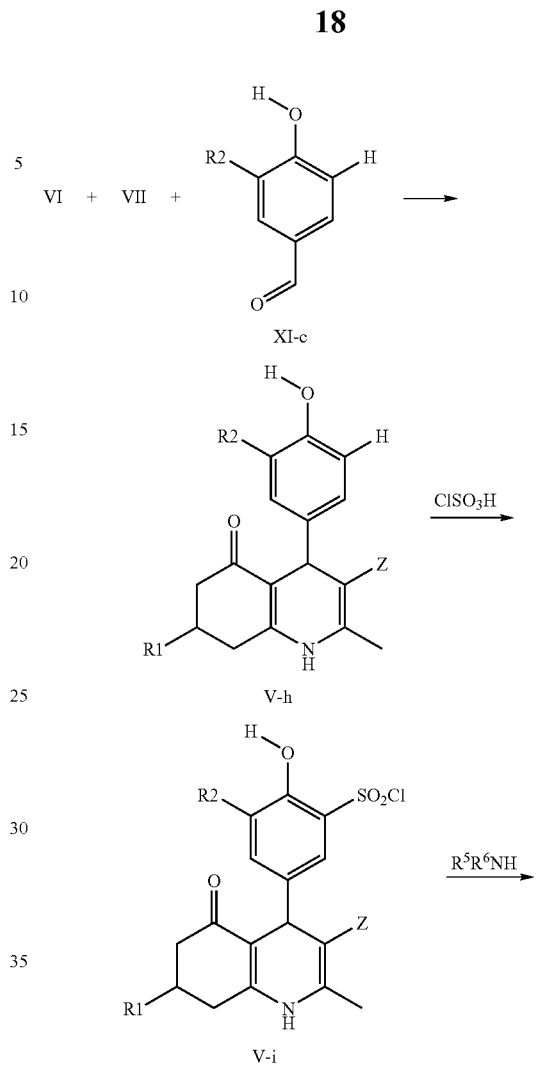

of phenols or anilines, which are well known to those skilled in the art. Thus, compounds of formula V-f-g—synthesized from compounds II and III and aldehydes XI by a Hantzsch-type cyclocondensation reaction—afford compounds of formula V-d-e upon treatment with bromine in a suitable solvent such as acetic acid, ethanol or dichloromethane or mixtures thereof, optionally in the presence of sodium acetate. Alternatively, N-bromosuccinimide in N,N-dimethylformamide or acetonitrile can be used to achieve this conversion. For example, see: J. Chem. Soc. Perkin Trans. 2 6 (2000) 1113-1118, J. Org. Chem. 44 (1979), 4733-4735.

Additionally, compounds of general formula V-j, wherein R³ is an aminosulfonyl group and X=O, can be obtained by reacting amines of general formula $R^5R^6NH$ with compounds of general formula V-i, optionally in the presence of a tertiary amine base such as triethylamine or DiPEA. Compounds V-i are obtained by chlorosulfonylation of compounds of general formula V-h. For examples in the literature concerning chlorosulfonylation of phenols, see: Tetrahedron 53 (1997) 4145-4158, Bioorg. Med. Chem. Lett. 13 (2003) 379-382.

The compounds of general formulas VI, VII and VIII are commercially available, documented in literature or readily prepared by those skilled in the art.

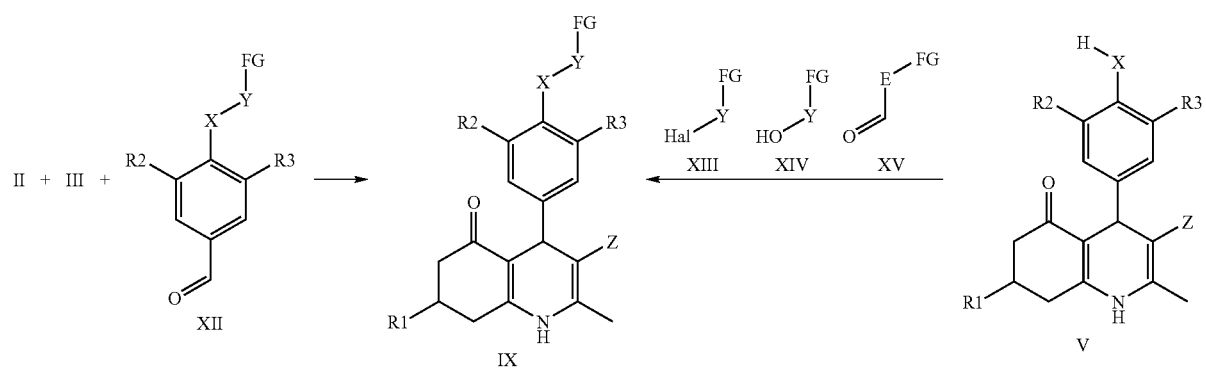

Y and E are alkyl, alkenyl, alkynyl or alkoxyalkyl groups

The 1,4,5,6,7,8-hexahydroquinoline derivatives of general formula IX can be prepared by the aforementioned Hantzsch-type cyclocondensation reaction between cyclohexanediones II, enamines III and aldehydes XII. Alternatively, alkylation of derivatives of general formula V with reagents XIII-XV—which are documented in literature, commercially available or readily prepared—can also provide derivatives IX by the same methods used for the preparation of compounds I-a-b from V-a-b, as described previously.

Benzaldehydes of general formula X and XI are commercially available or can be prepared according to literature procedures: J. Chem. Soc., Perkin Trans. 2 (2000) 1119-1124, J. Chem. Soc., Chem. Commun. 4 (1993) 419-420, Synth. Commun. 20 (1990) 2659-2666, Chem. Pharm. Bull. 34 (1986) 121-129, Indian J. Chem. Sect. B 20 (1981) 1010-1013, Monatsh. Chem. 106 (1975) 1191-1201, DE 1070162, J. Org. Chem. 23 (1958) 120, Tetrahedron Lett. 25 (1984), 2901-2904, J. Org. Chem. 25 (1960), 2053-2055, J. Chem. Soc., Perkin Trans. 2 (1992), 2235-2242. Additionally, benzaldehydes of general formula X-c wherein $R^2$ is bromide and X is N—H can be obtained by bromination of compounds of general formula XVI using the same procedures described for the conversion of compounds of general formula V-g to V-e.

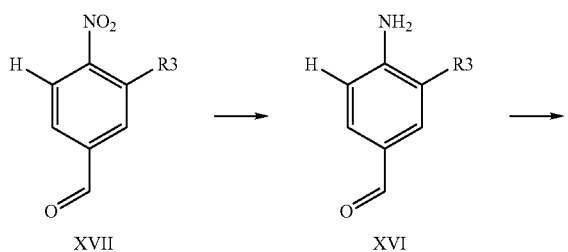

XVII    XVI

-continued

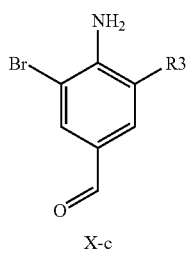

X-c

Compounds of general formula XVI can be obtained by the reduction of the nitro group in compounds of general formula XVII to the corresponding amino group. Typically, compounds XVII are treated with zinc and acetic acid in a suitable solvent such as THF or dioxane at temperatures between 0° C. and reflux temperature. Alternative methods include treatment with iron, $SnCl_2$, or hydrogen in the presence of a transition metal catalyst such palladium or platinum on charcoal, using methods and reagents well known to those skilled in the art.

Benzaldehydes of general formula X-d wherein $R^2$ is as previously defined $R^3$ is an aminosulfonyl group and X is O can be obtained by chlorosulfonylation of compounds of general formula XI-c followed by reaction with amines of general formula $R^5R^6NH$ using the same procedures described for the synthesis of compounds of general formula V-j from V-h via V-i. The hydroxyl group of compounds X-d can be triflated by art known methods to give compounds XVIII, which can undergo nucleophilic aromatic substitution with ammonia to yield benzaldehydes X-e. For related aromatic substitution reactions see: J. Med. Chem. 6 (1963) 272-275, Indian J. Chem. Sect. B 18 (1979), 88-90. Additionally, derivatives X-d can be converted to compounds of formula XIX, wherein PG is H or an optional protective group such as 4-nitrobenzyl or 2,5-dimethoxybenzyl, followed by art known Smiles rearrangement to give products of general formula X-e, after deprotection (if necessary). For examples of this type of rearrangement reactions, see: J. Org. Chem. 48 (1983) 5140-5143, Tetrahedron Lett. 30 (1989) 931-934, Tetrahedron 53 (1997) 11919-11928, Synth. Commun. 33 (2003) 2725-2736.

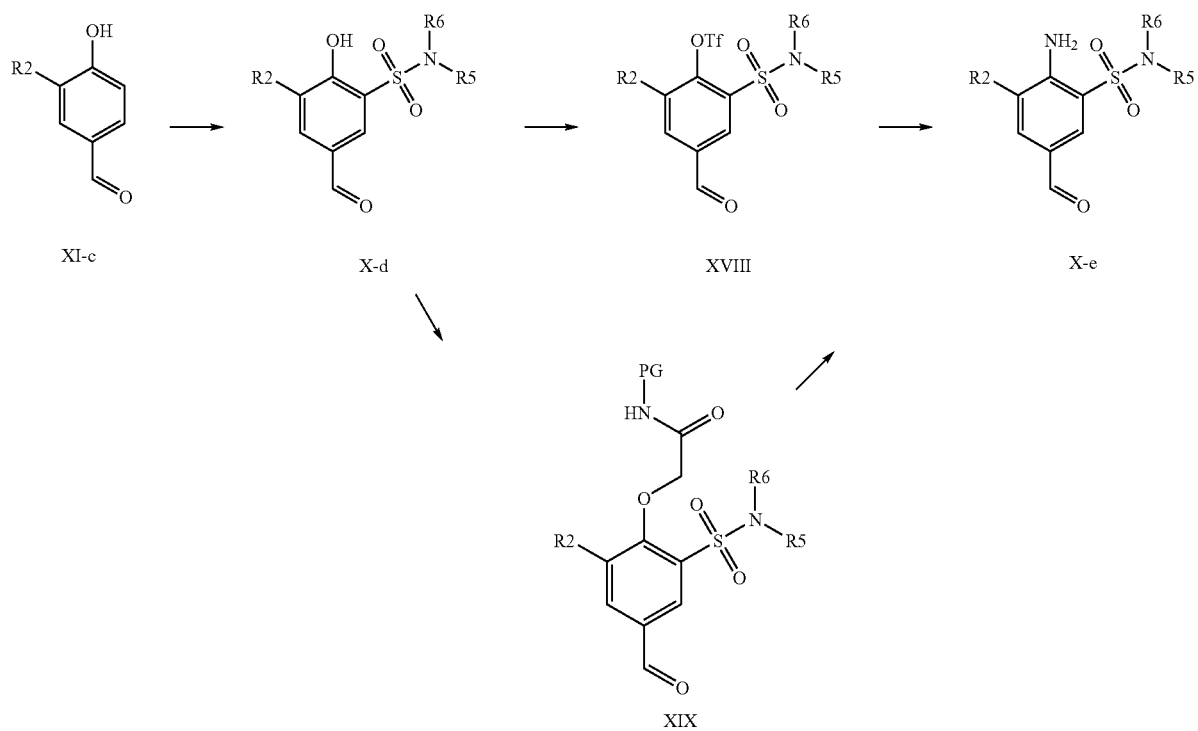

XI-c    X-d    XVIII    X-e

XIX

Benzaldehydes of general formula XII are prepared from the aforementioned aldehydes of formula X by alkylation with compounds of general formula XIII or XIV, in analogy with the preparation of aldehydes IV-a-b from X-a-b. Alternatively, benzaldehydes of formula XII, wherein X=NH, can be prepared by the same methods described for the conversion of derivatives X-d to X-e, using appropriately substituted amines of general formula $H_2N$—Y-FG in the reaction sequence.

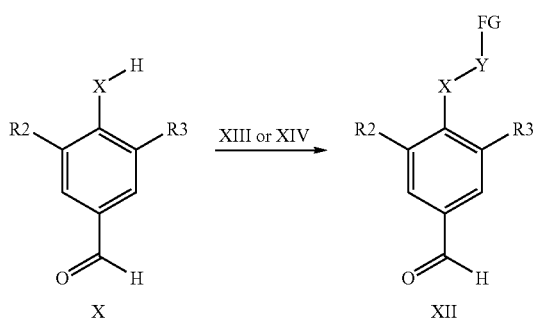

X    XII

The compounds of the present invention possess at least two chiral carbon atoms and may therefore be obtained as pure enantiomers, or as a mixture of enantiomers, or as a mixture of diastereomers. Methods for obtaining the pure enantiomers are well known in the art, e.g. crystallization of salts which are obtained from optically active acids and the racemic mixture, or chromatography using chiral columns. For separation of diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

The 2-methyl-4-phenyl-5-oxo-1,4,5,6,7,8-hexahydroquinoline derivatives of the invention were found to be agonists of the FSH receptor. Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of compound.

For measurement of binding, radioactive or fluorescent compounds may be used. As reference compound human recombinant FSH can be used.

In the alternative also competition binding assays may be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be increased, by the stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, C., Himmler, A. and Czernilofsky, A., (1995) Curr. Opin. Biotechnol. 6:574.

The present invention also relates to a pharmaceutical composition comprising a 2-methyl-4-phenyl-5-oxo-1,4,5,6,7,8-hexahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a 2-methyl-4-phenyl-5-oxo-1,4,5,6,7,8-hexahydroquinoline derivative having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of a 2-methyl-4-phenyl-5-oxo-1,4,5,6,7,8-hexahydroquinoline derivative having the general formula I for the manufacture of a medicament to be used for the treatment of infertility.

The invention is illustrated by the following examples.
General:

The following abbreviations are used in the examples: DMA=N,N-dimethylaniline, DiPEA=N,N-diisopropylethylamine, TFA=trifluoroacetic acid, HATU=O-(7-azabenzotriazole-1-yl)-N,N,N',N'-tetramethyluronium hexafluorophosphate, DMF=N,N-dimethylformamide, THF=tetrahydrofuran, EtOAc=ethyl acetate.

Unless stated otherwise, all final products of the examples below were lyophilized from water/1,4-dioxane mixtures, water/tert-butanol or water/acetonitrile mixtures. If the compound was prepared as TFA salt, TFA was added in an appropriate amount to the solvent mixture before lyophilization.

The names of the final products described in the examples were generated using the Beilstein Autonom program (version: 2.02.304).

The following analytical HPLC methods were used for determination of retention times:
Method 1: Column: 5 μm Luna C-18(2) 150×4.6 mm; flow: 1 ml/min; detection: 210 nm; column temperature: 40° C.; solvent A: $CH_3CN/H_2O=1/9$ (v/v); solvent B: $CH_3CN$; solvent C, 0.1 M aqueous trifluoroacetic acid; gradient: solvent A/B/C=75/20/5 to 15/80/5 (v/v/v) in 30.00 min, then constant for an additional 10.00 min at A/B/C=15/80/5 (v/v/v).
Method 2: Identical to method 1, except for the gradient used: Gradient: solvent A/B/C=95/0/5 to 15/80/5 (v/v/v) in 20.00 min, then constant for an additional 10.00 min at A/B/C=15/80/5 (v/v/v).

The diastereomeric ratio (Diast. ratio) was determined if baseline separation of the individual diastereomers was observed using the appropriate analytical HPLC method. Alternatively, the diastereomeric ratio was determined by $^1H$ NMR analysis when distinct signals corresponding to the diastereomers were identified. The reported diastereomeric ratios relate to the configurations of C-4 and C-7 of the 1,4,5,6,7,8-hexahydroquinoline core.

The following methods were used for preparative HPLC-purifications:
Method A: Column=Luna C-18. Gradient: 0.1% trifluoroacetic acid in $H_2O/CH_3CN$ (9/1, v/v)/$CH_3CN$=80/20 to 0/100 (v/v) in 30-45 min, depending on the ease of separation. Detection: 210 nm.
Method B: Column=Luna C-18. Gradient: $H_2O/CH_3CN$ (9/1, v/v)/$CH_3CN$=80/20 to 0/100 (v/v) in 30-45 min, depending on the ease of separation. Detection: 210 nm n.

Example 1

Furan-2-carboxylic acid {4-[2-bromo-4-(3-cyano-2-methyl-5-oxo-7-propyl-1,4,5,6,7,8-hexahydro-quinolin-4-yl)-6-ethoxy-phenoxy]-but-2-enyl}-amide (a). 4-(3-Bromo-5-ethoxy-4-hydroxy-phenyl)-2-methyl-5-oxo-7-propyl-1,4,5,6,7,8-hexahydro-quinoline-3-carbonitrile A mixture of 3-bromo-5-ethoxy-4-hydroxy-benzaldehyde (6 g), 3-aminocrotonitrile (2.01 g) and 5-propylcyclohexane-1,3-dione (3.8 g) in ethanol (20 ml) was stirred at 80° C. for 4 h. The reaction mixture was concentrated in vacuo and the residue was chromatographed on silica gel in heptane/EtOAc=1/1 (v/v) as eluent. Yield: 6.3 g. MS-ESI: $[M+H]^+$=445/447

(b). 4-[3-Bromo-4-(4-bromo-but-2-enyloxy)-5-ethoxy-phenyl]-2-methyl-5-oxo-7-propyl-1,4,5,6,7,8-hexahydro-quinoline-3-carbonitrile A mixture of 4-(3-bromo-5-ethoxy-4-hydroxy-phenyl)-2-methyl-5-oxo-7-propyl-1,4,5,6,7,8-hexahydro-quinoline-3-carbonitrile (3.04 g), 1,4-dibromobutene (11.68 g) and potassium carbonate (1.887 g) in dioxane (100 ml) was stirred at 80° C. for 5 h. The mixture was poured into water and extracted with dichloromethane. The organic layer was dried ($MgSO_4$), filtered and concentrated in vacuo. The residue was dissolved in acetonitrile, washed with petroleum ether and heptane to remove most of the excess of dibromobutene. The acetonitrile layer was concentrated in vacuo and the residue recrystallized from dichloromethane and heptane. Yield: 3.02 g. MS-ESI: $[M+H]^+$=579.2

(c). Mixture of 4-[4-(4-Azido-but-2-enyloxy)-3-bromo-5-ethoxy-phenyl]-2-methyl-5-oxo-7-propyl-1,4,5,6,7,8-hexahydro-quinoline-3-carbonitrile and 4-[4-(2-Azido-but-3-enyloxy)-3-bromo-5-ethoxy-phenyl]-2-methyl-5-oxo-7-propyl-1,4,5,6,7,8-hexahydroquinoline-3-carbonitrile A mixture of the compound obtained in example 1b (1.0 g) and sodium azide (0.34 g) in DMF (50 ml) was stirred for 2 h. The mixture was poured into water. The resulting precipitate was collected by filtration, washed with water and dried in vacuo. Yield: 914 mg: mixture of 2 regio-isomers. MS-ESI: $[M+H]^+$=540.2/542.2

(d). Mixture of 4-[4-(4-Amino-but-2-enyloxy)-3-bromo-5-ethoxy-phenyl]-2-methyl-5-oxo-7-propyl-1,4,5,6,7,8-hexahydro-quinoline-3-carbonitrile and 4-[4-(2-Amino-but-3-enyloxy)-3-bromo-5-ethoxy-phenyl]-2-methyl-5-oxo-7-propyl-1,4,5,6,7,8-hexahydroquinoline-3-carbonitrile To a solution of the crude mixture of regioisomeric compounds obtained in example 1c (0.914 g) in THF/dichloromethane (2/1 (v/v), 18 ml) was added water (2 ml) and resin bound triphenylphosphine (1.13 g, 3.0 mmol/g loading). The mixture was stirred at 40° C. for 8 h. The resin was filtered off and washed with dichloromethane and methanol. The combined organic layers were concentrated in vacuo. Yield: 0.8 g. mixture of 2 regio-isomers. MS-ESI: $[M+H]^+$=514.2/516.2

(e). Furan-2-carboxylic acid {4-[2-bromo-4-(3-cyano-2-methyl-5-oxo-7-propyl-1,4,5,6,7,8-hexahydro-quinolin-4-yl)-6-ethoxy-phenoxy]-but-2-enyl}-amide A solution of the products obtained in example 1d (88.8 mg), DiPEA (151 µl) and 2-furoyl chloride (34 µl) in dichloromethane (4 ml) was stirred for 17 h. The mixture was diluted with dichloromethane and washed with sat. aq. $NaHCO_3$. The organic layer was dried ($MgSO_4$), filtered and concentrated in vacuo. The residue was purified by preparative HPLC (Method B). Yield: 46.4 mg. MS-ESI: $[M+H]^+$=608.2/610.2; HPLC: $R_t$=19.45 min. (diast. 1) $R_t$=19.73 min. (diast. 2) (method 1). Diast. ratio: 4:1

Example 2

N-{4-[2-Bromo-4-(3-cyano-2-methyl-5-oxo-7-propyl-1,4,5,6,7,8-hexahydro-quinolin-4-yl)-6-ethoxy-phenoxy]-but-2-enyl}-isobutyramide A solution of the products described in example 1d (200 mg), DiPEA (339 µl) and isobutyryl chloride (81 µl) in dichloromethane (4 ml) was stirred for 17 h. The mixture was diluted with dichloromethane and washed with sat. aq. $NaHCO_3$. The organic layer was dried ($MgSO_4$), filtered and concentrated in vacuo. The residue was purified by preparative HPLC (Method B). Yield: 82 mg. MS-ESI: $[M+H]^+$=584.2/586.2; HPLC: $R_t$=19.41 min. (method 1). Diast. ratio: 4:1

Example 3

Cyclopropanecarboxylic acid {4-[2-bromo-4-(3-cyano-2-methyl-5-oxo-7-propyl-1,4,5,6,7,8-hexahydro-quinolin-4-yl)-6-ethoxy-phenoxy]-but-2-enyl}-amide The title compound was obtained from the mixture of compounds described in example 1d (88.8 mg), DiPEA (151 µl) and cyclopropanecarbonyl chloride (31 µl) according to the procedure described in example 2, and purified by preparative HPLC (Method B). The regioisomer (example 4) could also be isolated. Yield: 39 mg. MS-ESI: $[M+H]^+$=582.2/584.2; HPLC: $R_t$=18.75 min. (diast. 1) $R_t$=18.99 min. (diast. 2) (method 1). Diast. ratio: 4:1

Example 4

Cyclopropanecarboxylic acid {1-[2-bromo-4-(3-cyano-2-methyl-5-oxo-7-propyl-1,4,5,6,7,8-hexahydro-quinolin-4-yl)-6-ethoxy-phenoxymethyl]-allyl}-amide See example 3. The regioisomer of example 3 was also isolated by preparative HPLC (Method B). Yield: 18 mg. MS-ESI: $[M+H]^+=582.2/584.2$; HPLC: $R_t=20.05$ min. (diast. 1) $R_t=20.37$ min. (diast. 2) (method 1). Diast. ratio: 4:1

Example 5

N-{4-[2-Bromo-4-(3-cyano-2-methyl-5-oxo-7-propyl-1,4,5,6,7,8-hexahydro-quinolin-4-yl)-6-ethoxy-phenoxy]-but-2-enyl}-2-methoxy-acetamide The title compound was obtained from the mixture of compounds described in example 1d (88.8 mg), DiPEA (151 µl) and methoxyacetyl chloride (31 µl) according to the procedure described in example 2 and purified by preparative HPLC (Method B). Yield: 44.7 mg. MS-ESI: $[M+H]^+=586.4/588.4$; HPLC: $R_t=17.26$ min. (diast. 1) $R_t=17.56$ min. (diast. 2) (method 1). Diast. ratio: 4:1

Example 6

{4-[2-Bromo-4-(3-cyano-2-methyl-5-oxo-7-propyl-1,4,5,6,7,8-hexahydro-quinolin-4-yl)-6-ethoxy-phenoxy]-but-2-enyl}-carbamic acid ethyl ester The title compound was obtained from the mixture of compounds described in example 1d (88.8 mg), DiPEA (151 µl) and ethyl chloroformate (33 µl) according to the procedure described in example 2 and purified by preparative HPLC (Method B). The regioisomer (example 7) could also be isolated. Yield: 45.4 mg. MS-ESI: $[M+H]^+=586.2/588.2$. HPLC: $R_t=21.21$ min. (diast. 1) $R_t=21.52$ min. (diast. 2) (method 1). Diast. ratio: 4:1

Example 7

{1-[2-Bromo-4-(3-cyano-2-methyl-5-oxo-7-propyl-1,4,5,6,7,8-hexahydro-quinolin-4-yl)-6-ethoxy-phenoxymethyl]-allyl}-carbamic acid ethyl ester See example 6. The regioisomer of example 6 was isolated by preparative HPLC (Method B). Yield: 20 mg. MS-ESI: $[M+H]^+=586.2/588.2$; HPLC: $R_t=22.96$ min. (diast. 1) $R_t=23.33$ min. (diast. 2) (method 1). Diast. ratio: 4:1

Example 8

N-{1-[2-Bromo-4-(3-cyano-2-methyl-5-oxo-7-propyl-1,4,5,6,7,8-hexahydro-quinolin-4-yl)-6-ethoxy-phenoxymethyl]-allyl}-benzamide The title compound was obtained from the mixture of compounds described in example 1d (88.8 mg), DiPEA (151 µl) and benzoyl chloride (40 µl) according to the procedure described in example 2 and purified by preparative HPLC (Method B). Yield: 14.5 mg. MS-ESI: $[M+H]^+=618.4/620.4$; HPLC: $R_t=22.97$ min. (diast. 1) $R_t=23.27$ min. (diast. 2) (method 1). Diast. ratio: 3:1

Example 9

N-{1-[2-Bromo-4-(3-cyano-2-methyl-5-oxo-7-propyl-1,4,5,6,7,8-hexahydro-quinolin-4-yl)-6-ethoxy-phenoxymethyl]-allyl}-acetamide The title compound was from the mixture of compounds described in example 1d (88.8 mg), DiPEA (151 µl) and acetyl chloride (24 µl) according to the procedure described in example 2 and purified by preparative HPLC (Method B). Yield: 16.7 mg. MS-ESI: $[M+H]^+=556.2/568.2$; HPLC: $R_t=17.13$ min. (diast. 1) $R_t=17.44$ min. (diast. 2) (method 1). Diast. ratio: 3:1

Example 10

4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid (2-methoxy-ethyl)-amide (a). 4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid methyl ester A mixture of the compound described in example 1a (1.48 g), potassium carbonate (0.919 g) and methyl 4-bromocrotonate (4.759 g) in dioxane (60 ml) was stirred at 80° C. under a nitrogen atmosphere for 17 h. The mixture was diluted with dichloromethane and washed with water. The organic layer was dried (MgSO$_4$), filtered and concentrated in vacuo. The residue was chromatographed on silicagel in heptane/EtOAc (from 1/0 to 0/1) as eluent. Yield: 1.2 g. MS-ESI: $[M+H]^+=543.2/545.2$ (b). 4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid A solution of 4-[2-bromo-4-(3-cyano-2-methyl-5-oxo-7-propyl-1,4,5,6,7,8-hexahydroquinolin-4-yl)-6-ethoxy-phenoxy]-but-2-enoic acid methyl ester (1.2 g) in dioxane (100 ml) and 2N sodium hydroxide (2.2 ml) was stirred for 5 days. The mixture was poured into water and the pH was adjusted to 2 using 4N aqueous HCl. The resulting mixture was extracted with EtOAc. The organic layer was dried (MgSO$_4$), filtered and concentrated in vacuo. Yield: 1.5 g. MS-ESI: $[M+H]^+=529.2/531.2$ (c). 4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid (2-methoxy-ethyl)-amide A mixture of 4-[2-bromo-4-(3-cyano-2-methyl-5-oxo-7-propyl-1,4,5,6,7,8-hexahydroquinolin-4-yl)-6-ethoxy-phenoxy]-but-2-enoic acid (0.1 g), HATU (0.108 g), DiPEA (165 µl) and 2-methoxyethylamine (25 µl) in dichloromethane was stirred for 2 h. The reaction mixture was diluted with water and extracted with EtOAc. The organic layer was dried (MgSO$_4$), filtered and concentrated in vacuo. The residue was purified by preparative HPLC (Method B). Yield: 65.5 mg. MS-ESI: $[M+H]^+=586.4/588.4$; HPLC: $R_t=16.39$ min. (method 1). Diast. ratio: 5:1

Example 11

4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid isopropyl-methyl-amide The title compound was obtained from the compound described in example 10b (100 mg), DiPEA (165 µl), HATU (108 mg) and isopropyl-methyl-amine (29 μl) according to the procedure described in example 10c. Yield: 65 mg. MS-ESI: [M+H]$^+$=584.4/586.4; HPLC: R$_t$=19.27 min. (diast. 1) R$_t$=19.54 min. (diast. 2) (method 1). Diast. ratio: 5:1

Example 12

4-[2-Bromo-4-(3-cyano-2-methyl-5-oxo-7-propyl-1,4,5,6,7,8-hexahydro-quinolin-4-yl)-6-ethoxy-phenoxy]-but-2-enoic acid (pyridin-2-ylmethyl)-amide The title compound was obtained from the compound described in example 10b (100 mg), DiPEA (165 μl), HATU (108 mg) and 2-picolylamine (29 μl) according to the procedure described in example 10c. The residue was purified by preparative HPLC (Method A). Yield: 63 mg (as TFA salt). MS-ESI: [M+H]$^+$=619.4/621.4; HPLC: R$_t$=9.92 min. (method 1). Diast. ratio: 5:1

Example 13

N-{4-[2-Bromo-4-(3-cyano-2-methyl-5-oxo-7-propyl-1,4,5,6,7,8-hexahydro-quinolin-4-yl)-6-ethoxy-phenoxy]-butyl}-isobutyramide (a). 4-[3-Bromo-4-(4-bromo-butoxy)-5-ethoxy-phenyl]-2-methyl-5-oxo-7-propyl-1,4,5-6,7,8-hexahydro-quinoline-3-carbonitrile A mixture of the compound described in example 1a (2.23 g), 1,4-dibromobutane (8.65 g) and potassium carbonate (3 g) in DMF (25 ml) was stirred at 60° C. for 2 h. The mixture was cooled to room temperature and washed with heptane to remove most of the excess of dibromobutane. The DMF layer was diluted with water and the resulting mixture extracted with EtOAc. The organic layer was dried (MgSO$_4$), filtered and concentrated in vacuo. The residue was chromatographed on silicagel in heptane/EtOAc (from 4/1 to 1/2) as eluent. Yield: 2.23 g. MS-ESI: [M+H]$^+$=581.1

(b). 4-[4-(4-Amino-butoxy)-3-bromo-5-ethoxy-phenyl]-2-methyl-5-oxo-7-propyl-1,4,-5,6,7,8-hexahydro-quinoline-3-carbonitrile To a solution of the product of step a (2 g) in dioxane (60 ml) was added conc. aq. NH$_4$OH (40 ml). The mixture was stirred in an autoclave at 80° C. for 17 h, and then concentrated in vacuo. Yield: 2.21 g HBr salt). MS-ESI: [M+H]$^+$=516.4/518.4

(c). N-{4-[2-Bromo-4-(3-cyano-2-methyl-5-oxo-7-propyl-1,4,5,6,7,8-hexahydro-quinolin-4-yl)-6-ethoxy-phenoxy]-butyl}-isobutyramide A mixture of the product of step b (117 mg), triethylamine (81 μl) and isobutyrylchloride (24 μl) in dichloromethane (3 ml) was stirred for 17 h. The mixture was diluted with dichloromethane and washed with 0.5N aqueous HCl. The organic layer was dried (MgSO$_4$), filtered and concentrated in vacuo. The residue was chromatographed on silicagel in heptane/EtOAc (from 1/0 to 0/1) as eluent. Yield: 69 mg. MS-ESI: [M+H]$^+$=610.4/612.4; HPLC: R$_t$=19.45 min. (method 1). Diast. ratio: 5:1

Example 14

Ethanesulfonic acid {4-[2-bromo-4-(3-cyano-2-methyl-5-oxo-7-propyl-1,4,5,6,7,8-hexahydro-quinolin-4-yl)-6-ethoxy-phenoxy]-butyl}-amide The title compound was obtained from the compound described in example 13b (150 mg), triethylamine (104 μl) and ethanesulfonyl chloride (28 μl) according to the procedure described in example 13c. Yield: 99 mg. MS-ESI: [M+H]$^+$=608.2/610.2; HPLC: R$_t$=19.32 min. (diast. 1) R$_t$=19.57 min. (diast. 2) (method 1). Diast. ratio: 4:1

Example 15

Cyclopropanecarboxylic acid {3-[2-bromo-4-(3-cyano-2-methyl-5-oxo-7-propyl-1,4,5,6,7,8-hexahydro-quinolin-4-yl)-6-ethoxy-phenoxy]-propyl}-amide (a). 4-[3-Bromo-4-(3-bromo-propoxy)-5-ethoxy-phenyl]-2-methyl-5-oxo-7-propyl-1,4,5,6,7,8-hexahydro-quinoline-3-carbonitrile The title compound was obtained from the compound described in example 1a (2 g), 1,3-dibromopropane (3.67 ml) and potassium carbonate (2.49 g) according to the procedure described in example 13a. Yield: 2.47 g. MS-ESI: [M+H]$^+$=567.2

(b). 4-[4-(3-Amino-propoxy)-3-bromo-5-ethoxy-phenyl]-2-methyl-5-oxo-7-propyl-1,4,5,6,7,8-hexahydro-quinoline-3-carbonitrile The title compound was obtained from the product of step a (2.37 g) and conc. aq. NH$_4$OH (40 ml) according to the procedure described in example 13b. Yield: 2.45 g (HBr salt). MS-ESI: [M+H]$^+$=502.3/504.3

(c). Cyclopropanecarboxylic acid {3-[2-bromo-4-(3-cyano-2-methyl-5-oxo-7-propyl-1,4,5,6,7,8-hexahydro-quinolin-4-yl)-6-ethoxy-phenoxy]-propyl}-amide A mixture of the product of step b (165 mg), triethylamine (118 μl) and cyclopropanecarbonyl chloride (31 μl) in dichloromethane (2 ml) was stirred for 17 h. The reaction mixture was diluted with EtOAc and washed with 0.5N aqueous HCl. The organic layer was dried (MgSO$_4$), filtered and concentrated in vacuo. The residue was chromatographed on silicagel in heptane/EtOAc (from 3/1 to 0/1) as eluent.
Yield: 111.2 mg. MS-ESI: [M+H]$^+$=570.4/572.4; HPLC: R$_t$=18.23 min. (method 1). Diast. ratio: 5:1

Example 16

N-{5-[2-Bromo-4-(3-cyano-2-methyl-5-oxo-7-propyl-1,4,5,6,7,8-hexahydro-quinolin-4-yl)-6-ethoxy-phenoxy]-pentyl}-acetamide (a). 4-[3-Bromo-4-(5-chloro-pentyloxy)-5-ethoxy-phenyl]-2-methyl-5-oxo-7-propyl-1,4,5,6,7,8-hexahydro-quinoline-3-carbonitrile The title compound was obtained from the compound described in example 1a (2 g), 1,5-dichloropentane (4.76 ml)

and potassium carbonate (2.49 g) according to the procedure described in example 13a. Yield: 2.1 g. MS-ESI: [M+H]⁺= 549.2/551.2

(b). 4-[4-(5-Amino-pentyloxy)-3-bromo-5-ethoxy-phenyl]-2-methyl-5-oxo-7-propyl-1,4,5,6,7,8-hexahydro-quinoline-3-carbonitrile The title compound was obtained from the product of step a (2.0 g) and conc. aq. NH₄OH (40 ml) according to the procedure described in example 13b. Yield: 2.1 g (HCl salt). MS-ESI: [M+H]⁺=530.3/532.3

(c). N-{5-[2-Bromo-4-(3-cyano-2-methyl-5-oxo-7-propyl-1,4,5,6,7,8-hexahydroquinolin-4-yl)-6-ethoxy-phenoxy]-pentyl}-acetamide The title compound was obtained from the product of step b (147.5 mg), triethylamine (108 µl) and acetyl chloride (22 µl) according to the procedure described in example 15c. Yield: 53.6 mg. MS-ESI: [M+H]⁺=572.4/574.4; HPLC: $R_t$=17.44 min. (diast. 1) $R_t$=17.75 min. (diast. 2) (method 1). Diast. ratio: 5:1

Example 17

N-{5-[2-Bromo-4-(3-cyano-2-methyl-5-oxo-7-propyl-1,4,5,6,7,8-hexahydro-quinolin-4-yl)-6-ethoxy-phenoxy]-pentyl}-2-methoxy-acetamide The title compound was obtained from the compound described in example 16b (147.5 mg), triethylamine (108 µl) and methoxyacetyl chloride (28 µl) according to the procedure described in example 15c. Yield: 88.5 mg. MS-ESI: [M+H]⁺=602.4/604.4; HPLC: $R_t$=18.87 min. (diast. 1) $R_t$=19.20 min. (diast. 2) (method 1). Diast. ratio: 5:1

Example 18

Furan-2-carboxylic acid {4-[2-bromo-4-(3-cyano-2-methyl-5-oxo-7-propyl-1,4,5,6,7,8-hexahydro-quinolin-4-yl)-6-ethoxy-phenoxy]-butyl}-amide The title compound was obtained from the compound described in example 13b (117 mg), triethylamine (81 µl) and 2-furoyl chloride (23 µl) according to the procedure described in example 13c. Yield: 85.7 mg. MS-ESI: [M+H]⁺=610.4/612.4; HPLC: $R_t$=19.66 min. (method 1). Diast. ratio: 5:1

Example 19

N-{2-[2-Bromo-4-(3-cyano-2-methyl-5-oxo-7-propyl-1,4,5,6,7,8-hexahydro-quinolin-4-yl)-6-ethoxy-phenoxy]-ethyl}-methanesulfonamide (a). 4-[3-Bromo-5-ethoxy-4-(2-hydroxy-ethoxy)-phenyl]-2-methyl-5-oxo-7-propyl-1,4,5,6,7,8-hexahydro-quinoline-3-carbonitrile A mixture of the compound described in example 1a (4 g), potassium carbonate (3.73 g) and 2-bromoethanol (1.274 ml) in DMF (30 ml) was stirred at 60° C. for 3 h. The reaction mixture was diluted with water and extracted twice with EtOAc. The combined organic layers were dried (MgSO₄), filtered and concentrated in vacuo. The residue was chromatographed on silicagel in heptane/EtOAc (from 1/1 to 0/1) as eluent. Yield: 3.1 g. MS-ESI: [M+H]⁺=489.4/491.4

(b). Methanesulfonic acid 2-[2-bromo-4-(3-cyano-2-methyl-5-oxo-7-propyl-1,4,5,6,7,8-hexahydro-quinolin-4-yl)-6-ethoxy-phenoxy]-ethyl ester A mixture of the product of step a (2.9 g), triethylamine (2.46 ml) and methanesulfonyl chloride (550 µl) in dichloromethane (50 ml) was stirred for 17 h. The mixture was extracted with 0.5N aqueous HCl. The organic layer was dried (MgSO₄), filtered and concentrated in vacuo. The residue was chromatographed on silicagel in dichloromethane/methanol from (1/0 to 95/5) as eluent. Yield: 3.38 g. MS-ESI: [M+H]⁺=567.2/569.2

(c). 4-[4-(2-Amino-ethoxy)-3-bromo-5-ethoxy-phenyl]-2-methyl-5-oxo-7-propyl-1,4,5,6,7,8-hexahydro-quinoline-3-carbonitrile A mixture of the product of step b (3.38 g) and conc. aq. NH₄OH (60 ml) in dioxane (90 ml) was stirred at 80° C. in an autoclave for 17 h. The mixture was concentrated in vacuo. Yield: 3.82 g (MeSO₃H salt). MS-ESI: [M+H]⁺=488.2/490.2

(d). N-{2-[2-Bromo-4-(3-cyano-2-methyl-5-oxo-7-propyl-1,4,5,6,7,8-hexahydroquinolin-4-yl)-6-ethoxy-phenoxy]-ethyl}-methanesulfonamide A mixture of the product of step c (130.7 mg), triethylamine (93 µl) and methanesulfonyl chloride 21 µl in dichloromethane (3 ml) was stirred for 17 h. The mixture was diluted with dichloromethane and washed with 0.5N aqueous HCl. The organic layer was dried (MgSO₄), filtered and concentrated in vacuo. The residue was purified by preparative HPLC (Method B). Yield: 57.1 mg. MS-ESI: [M+H]⁺=566.0/568.0; HPLC: $R_t$=12.49 min. (method 1). Diast. ratio: 4:1

Example 20

Propane-2-sulfonic acid {6-[2-bromo-4-(3-cyano-2-methyl-5-oxo-7-propyl-1,4,5,6,7,8-hexahydro-quinolin-4-yl)-6-ethoxy-phenoxy]-hexyl}-amide (a). 4-[3-Bromo-4-(6-bromo-hexyloxy)-5-ethoxy-phenyl]-2-methyl-5-oxo-7-propyl-1,4,5,6,7,8-hexahydro-quinoline-3-carbonitrile The title compound was obtained from the compound described in example 1a (1 g), 1,6-dibromohexane (2.78 ml) and potassium carbonate (1.24 g) according to the procedure described in example 13a. Yield: 0.93 g. MS-ESI: [M+H]⁺= 607.4/609.4

(b). 4-[4-(6-Amino-hexyloxy)-3-bromo-5-ethoxy-phenyl]-2-methyl-5-oxo-7-propyl-1,4,5,6,7,8-hexahydro-quinoline-3-carbonitrile The title compound was obtained from the product of step a (0.93 g) and conc. aq. NH₄OH (20 ml) according to the procedure described in example 13b. Yield: 1.08 g (HBr salt). MS-ESI: [M+H]⁺=544.4/546.4

(c). Propane-2-sulfonic acid {6-[2-bromo-4-(3-cyano-2-methyl-5-oxo-7-propyl-1,4,5,6,7,8-hexahydro-quinolin-4-yl)-6-ethoxy-phenoxy]-hexyl}-amide The title compound was obtained from the compound described in step b (134 mg), triethylamine (89 µl) and isopropylsulfonyl chloride (29 μl) according to the procedure described in example 13c. Yield: 22.5 mg. MS-ESI: [M+H]$^+$=650.4/652.4; HPLC: R$_t$=20.20 min. (diast. 1) R$_t$=20.55 min. (diast. 2) (method 1). Diast. ratio: 5:1

Example 21

4-{4-[2-(2-Amino-ethoxy)-ethoxy]-3-bromo-5-ethoxy-phenyl}-2-methyl-5-oxo-7-propyl-1,4,5,6,7,8-hexahydro-quinoline-3-carbonitrile (a). 4-{3-Bromo-5-ethoxy-4-[2-(2-hydroxy-ethoxy)-ethoxy]-phenyl}-2-methyl-5-oxo-7-propyl-1,4,5,6,7,8-hexahydro-quinoline-3-carbonitrile Alkylation of the compound described in example 1a (5 g) with (2-chloroethoxy)-ethanol (1.42 ml) was performed according to the method described in example 10a. The residue was chromatographed on silica gel in heptane/EtOAc as eluent.
Yield: 3.03 g. MS-ESI: [M+H]$^+$=533.2/535.2

(b). Methanesulfonic acid 2-{2-[2-bromo-4-(3-cyano-2-methyl-5-oxo-7-propyl-1,4,5,6,7,8-hexahydro-quinolin-4-yl)-6-ethoxy-phenoxy]-ethoxy}-ethyl ester The title compound was obtained analogously to the method described in example 19b starting from the compound described in example 21a (3.0 g) and methanesulfonyl chloride (522 μl). Yield: 2.98 g. MS-ESI: [M+H]$^+$=611.4/613.4

(c). 4-{4-[2-(2-Amino-ethoxy)-ethoxy]-3-bromo-5-ethoxy-phenyl}-2-methyl-5-oxo-7-propyl-1,4,5,6,7,8-hexahydro-quinoline-3-carbonitrile The title compound was obtained analogously to the method described in example 19c starting from the compound described in step b (2.98 g) which yielded 3.0 g of the title compound (MeSO$_3$H salt). A small amount (214 mg) was purified by preparative HPLC (Method A). Yield: 221.7 mg (TFA salt). MS-ESI: [M+H]$^+$=532.2/534.2; HPLC: R$_t$=15.39 min (method 2). Diast. ratio: 5:1

Example 22

Cyclopropanecarboxylic acid (2-{2-[2-bromo-4-(3-cyano-2-methyl-5-oxo-7-propyl-1,4,5,6,7,8-hexahydro-quinolin-4-yl)-6-ethoxy-phenoxy]-ethoxy}-ethyl)-amide The title compound was obtained analogously to the method described in example 19d starting from the crude compound (MeSO$_3$H salt) described in example 21c (214 mg) and cyclopropanecarbonyl chloride (37 μl), in the presence of triethylamine (141 μl). The residue was purified by preparative HPLC (Method B). Yield: 165 mg. MS-ESI: [M+H]$^+$=600.4/602.4; HPLC: R$_t$=22.40 min (method 2). Diast. ratio: 8:1

Example 23

3-Bromo-5-(3-cyano-2-methyl-5-oxo-7-propyl-1,4,5,6,7,8-hexahydro-quinolin-4-yl)-2-[2-(2-hydroxy-ethoxy)-ethoxy]-N,N-dimethyl-benzenesulfonamide (a). 4-(3-Bromo-4-hydroxy-phenyl)-2-methyl-5-oxo-7-propyl-1,4,5,6,7,8-hexahydroquinoline-3-carbonitrile The reaction of 3-bromo-4-hydroxy-benzaldehyde (13.07 g) with 3-aminocrotonitril (5.34 g) and 5-propylcyclohexane-1,3-dione (10.02 g) was performed according to the method described in example 1a. Yield: 20.25 g. MS-ESI: [M+H]$^+$=401/403

(b). 3-Bromo-5-(3-cyano-2-methyl-5-oxo-7-propyl-1,4,5,6,7,8-hexahydro-quinolin-4-yl)-2-hydroxy-benzenesulfonyl chloride At −10° C. and under a nitrogen atmosphere, the compound described in example 23a (20.25 g) was added portion wise during 1 h to ClSO$_3$H (47 ml). After stirring at −10° C. for 1 h, the reaction mixture was allowed to warm (room temperature) and stirring was continued for another 17 h. The reaction mixture was poured on crushed ice (800 ml) and extracted several times with EtOAc. The combined organic layers were dried (MgSO$_4$), filtered and concentrated in vacuo. The residue was recrystallized from EtOAc. Yield: 23.7 g. MS-ESI: [M+H]$^+$=499.0/501.0

(c). 3-Bromo-5-(3-cyano-2-methyl-5-oxo-7-propyl-1,4,5,6,7,8-hexahydro-quinolin-4-yl)-2-hydroxy-N,N-dimethyl-benzenesulfonamide Dimethylamine was bubbled through a suspension of the compound described in example 23b (4.1 g) in dioxane (85 ml) for 30 min. After stirring for 17 h, the reaction mixture was diluted with EtOAc and washed with water. During extraction the title compound crystallized in the water layer. The title compound was obtained by filtration. Yield: 2.19 g. MS-ESI: [M+H]$^+$=508.2/510.2

(d). 3-Bromo-5-(3-cyano-2-methyl-5-oxo-7-propyl-1,4,5,6,7,8-hexahydro-quinolin-4-yl)-2-[2-(2-hydroxy-ethoxy)-ethoxy]-N,N-dimethyl-benzenesulfonamide Alkylation of the compound described in example 23c (740 mg) with 2-(2-chloro ethoxy)-ethanol (185 μl) was performed according to the method described in example 10a. Yield: 35.6 mg. MS-ESI: [M+H]$^+$=596/598; HPLC: R$_t$=14.73 min (method 1)

Example 24

4-{3-Bromo-4-[2-(2-hydroxy-ethoxy)-ethoxy]-5-isopropoxy-phenyl}-2-methyl-5-oxo-7-propyl-1,4,5,6,7,8-hexahydro-quinoline-3-carbonitrile (a). 3-Bromo-5-hydroxy-4-(4-nitro-benzyloxy)-benzaldehyde A mixture of 3-bromo-4,5-dihydroxy-benzaldehyde (2 g), 4-nitrobenzylbromide (2 g), lithium carbonate (680 mg) and a small amount of tetrabutylammonium iodide (ca 50 mg) in DMF (15 ml) was stirred at 60° C. for 4 h. The mixture was diluted with EtOAc and washed with water. The organic layer was dried (MgSO$_4$), filtered and concentrated in vacuo. Yield: 2.82 g. MS-ESI: [M+H]$^+$=352.0/354.0

(b). 3-Bromo-5-isopropoxy-4-(4-nitro-benzyloxy)-benzaldehyde

A mixture of the product of step a (2.82 g), isopropyl iodide (1.6 ml) and potassium carbonate (2.21 g) in DMF (25 ml) was stirred at 60° C. for 4 h. The mixture was diluted with EtOAc and washed with water. The organic layer was dried (MgSO$_4$), filtered and concentrated in vacuo. Yield: 1.66 g. MS-ESI: [M+H]$^+$=394.0/396.0

(c). 4-[3-Bromo-5-isopropoxy-4-(4-nitro-benzyloxy)-phenyl]-2-methyl-5-oxo-7-propyl-1,4,5,6,7,8-hexahydro-quinoline-3-carbonitrile A mixture of the product of step b (1.06 g), 3-aminocrotonitrile (221 mg) and 5-propylcyclohexane-1,3-dione (415 mg) in ethanol (20 ml) was stirred at 80° C. for 17 h. The reaction mixture was concentrated in vacuo and the residue was chromatographed on silica gel in heptane/EtOAc=1/1 (v/v) as eluent. Yield: 750 mg. MS-ESI: [M+H]$^+$=594.4/596.4

(d). 4-(3-Bromo-4-hydroxy-5-isopropoxy-phenyl)-2-methyl-5-oxo-7-propyl-1,4,5,6,-7,8-hexahydroquinoline-3-carbonitrile To a solution of the product isolated in step c (750 mg) and acetic acid (1.5 ml) in THF (50 ml) was added zinc dust (1.5 g) under vigorous stirring. The mixture was stirred for 2 h and then filtered. The mixture was diluted with EtOAc and washed with sat. aq. NaHCO$_3$. The organic layer was dried (MgSO$_4$), filtered and concentrated in vacuo.
Yield: 720 mg. MS-ESI: [M+H]$^+$=457.6/459.6

(e). 4-{3-Bromo-4-[2-(2-hydroxy-ethoxy)-ethoxy]-5-isopropoxy-phenyl}-2-methyl-5-oxo-7-propyl-1,4,5,6,7,8-hexahydro-quinoline-3-carbonitrile A mixture of the crude compound described in step d (100 mg), 2-(2-chloroethoxy)ethanol (27 µl), potassium carbonate (90 mg) and a catalytic amount of tetrabutylammonium iodide in DMF (3 ml) was stirred for 20 h. The mixture was diluted with EtOAc and washed with water. The organic layer was dried (MgSO$_4$), filtered and concentrated in vacuo. The residue was chromatographed on silicagel in heptane/EtOAc (from 1/0 to 0/1) as eluent. Yield: 29 mg. MS-ESI: [M+H]$^+$=547.2/549.2; HPLC: R$_t$=18.25 min. (method 1). Diast. ratio: 3:1

Example 25

4-{3-Bromo-5-ethoxy-4-[2-(2-hydroxy-ethoxy)-ethoxy]-phenyl}-2-methyl-3-nitro-7-propyl-4,6,7,8-tetrahydro-1H-quinolin-5-one (a). 1-Nitro-propan-2-one To a cooled solution of nitromethane (1.73 ml) in THF (50 ml) was added sodium hydride (1.28 g). After stirring for 20 min., the mixture is added to a solution of acetylimidazole (2.72 g) in THF (50 ml) and heated at reflux for 17 h. A precipitate formed, which was collected by filtration. The solid was dissolved in water, and the pH was adjusted to 3. The aqueous layer was extracted with EtOAc 3 times. The organic layer was dried (MgSO$_4$), filtered and concentrated in vacuo. Yield: 1.84 g.

(b). 1-Methyl-2-nitro-vinylamine

A mixture of 1-nitro-propan-2-one (1.6 g) and ammonium acetate (1.3 g) in toluene (25 ml) was heated at reflux for 17 h. Water was removed from the reaction mixture using a Dean-Stark apparatus. The reaction mixture was concentrated in vacuo. The residue was chromatographed on silicagel in heptane/EtOAc (from 1/0 to 0/1) as eluent. Yield: 1.07 g.

(c). 4-(3-Bromo-5-ethoxy-4-hydroxy-phenyl)-2-methyl-3-nitro-7-propyl-4,6,7,8-tetra-hydro-1H-quinolin-5-one A mixture of 1-methyl-2-nitro-vinylamine (1 g), 5-propylcyclohexane-1,3-dione (1.61 g) and 3-bromo-5-ethoxy-4-hydroxy-benzaldehyde (2.57 g) in ethanol (50 ml) was stirred at reflux for 17 h. The reaction mixture was concentrated in vacuo. The residue was dissolved in dichloromethane. A precipitate formed, which was collected by filtration. The solid was chromatographed on silicagel in heptane/EtOAc (from 1/0 to 0/1) as eluent. Yield: 2.8 g. MS-ESI: [M+H]$^+$=465.0/467.0

(d). 4-{3-Bromo-5-ethoxy-4-[2-(2-hydroxy-ethoxy)-ethoxy]-phenyl}-2-methyl-3-nitro-7-propyl-4,6,7,8-tetrahydro-1H-quinolin-5-one A mixture of the product described in step c (120 mg), 2-(2-Chloro-ethoxy)-ethanol (39 mg) and potassium carbonate (110 mg) in DMF (1 ml) was stirred at 60° for 17 h. The mixture was diluted with dichloromethane and washed with 1N aqueous HCl. The organic layer was dried (MgSO$_4$), filtered and concentrated in vacuo. The residue was purified by preparative HPLC (Method B). Yield: 21.7 mg. MS-ESI: [M+H]$^+$=553.0/555.0; HPLC: R$_t$=16.12 min. (diast. 1) R$_t$=16.46 min. (diast. 2) (method 1). Diast. ratio: 4:1

Example 26

3-Bromo-5-(3-cyano-2-methyl-5-oxo-7-propyl-1,4,5,6,7,8-hexahydro-quinolin-4-yl)-2-(2-hydroxy-ethoxy)-N,N-dimethyl-benzenesulfonamide A mixture of the compound described in example 23c (203 mg), 2-bromo ethanol (29.5 µl), potassium carbonate (187 mg) and potassium iodide (8 mg) in DM (10 ml) was stirred at 60° C. for 17 h. The mixture was diluted with EtOAc and washed with water. The organic layer was dried (MgSO$_4$), filtered and concentrated in vacuo. The residue was purified by preparative HPLC (Method B). Yield: 17 mg. MS-ESI: [M+H]$^+$=552.2/554.2; HPLC: R$_t$=14.56 min. (method 1)

Example 27

4-[3-Bromo-5-ethoxy-4-(2-hydroxy-ethoxy)-phenyl]-2-methyl-5-oxo-7-propyl-1,4,5,6,7,8-hexahydro-quinoline-3-carbonitrile The title compound was obtained from the compound described in example 1a (350 mg), 2-bromo ethanol (111l), potassium carbonate (326 mg) and potassium iodide (8 mg) according to the procedure described in example 26. Yield: 272.3 mg. MS-ESI: [M+H]$^+$=489.2/491.2; HPLC: R$_t$=21.15 min. (method 2). Diast. ratio: 6:1

Example 28

4-[3-Bromo-5-ethoxy-4-(4-hydroxy-but-2-enyloxy)-phenyl]-2-methyl-5-oxo-7-propyl-1,4,5,6,7,8-hexahydro-quinoline-3-carbonitrile To a solution of the compound described in example 1b (150 mg) in dioxane (2.5 ml) and water (2.5 ml) was added calcium carbonate (130 mg). The mixture was stirred under a nitrogen atmosphere at 100° C. for 4 h. The mixture was diluted with EtOAc and washed with 1N aqueous HCl. The organic layer was dried (MgSO$_4$), filtered and concentrated in vacuo. The residue was chromatographed on silicagel in heptane/EtOAc (from 1/0 to 0/1) as eluent. Yield: 95 mg. MS-ESI: [M+H]$^+$=515.2/517.2; HPLC: R$_t$=16.19 min. (method 1)

Example 29

3-Bromo-5-(3-cyano-2-methyl-5-oxo-7-propyl-1,4,5,6,7,8-hexahydro-quinolin-4-yl)-2-(2-methoxy-ethoxy)-N,N-dimethyl-benzenesulfonamide A mixture of the compound described in example 23c (200 mg), 2-bromoethyl methyl ether (39 µl), potassium carbonate (109 mg) and potassium iodide (20 mg) in DMF (5 ml) was stirred at 60° C. for 17 h. The mixture was diluted with EtOAc and washed with water. The organic layer was dried (MgSO$_4$), filtered and concentrated in vacuo. The residue was chromatographed on aluminum oxide in EtOAc as eluent. Yield: 46.8 mg. MS-ESI: [M+H]$^+$=566.0/568.0; HPLC: R$_t$=19.84 min. (method 1)

Example 30

3-Bromo-5-(3-cyano-2-methyl-5-oxo-7-propyl-1,4,5,6,7,8-hexahydro-quinolin-4-yl)-2-[2-(2-methoxy-ethoxy)-ethoxy]-N,N-dimethyl-benzenesulfonamide A mixture of the compound described in example 23c (202 mg), 2-(2-methoxyethoxy)ethanol (78 µl), diethyl azodicarboxylate (DEAD) (75 µl) and resin bound triphenyl phosphine (237 mg (1.69 mmol/g loading) in dichloromethane (3 ml) and THF (0.75 ml) was stirred for 17 h. The resin was filtered off and washed with methanol. The combined organic layers were dried (MgSO$_4$), filtered and concentrated in vacuo. The residue was purified by preparative HPLC (Method B). Yield: 22.5 mg. MS-ESI: [M+H]$^+$=610.2/612.2; HPLC: R$_t$=19.13 min. (method 1)

Example 31

4-[3-Bromo-4-(2-methoxy-ethylamino)-5-(morpholine-4-sulfonyl)-phenyl]-2-methyl-5-oxo-7-propyl-1,4,5,6,7,8-hexahydro-quinoline-3-carbonitrile (a). 3-Bromo-5-chlorosulfonyl-4-fluoro-benzoic acid 3-Bromo-4-fluoro-benzoic acid (2.0 g) was dissolved in chlorosulfonic acid (97%, 35 ml) and heated at 170° C. for 72 h. The reaction mixture was cooled to RT and added dropwise to an ice-water mixture. Extraction with EtOAc, drying (MgSO$_4$) and concentration in vacuo gave the desired compound. Yield: 2.5 g.

(b). 3-Bromo-4-fluoro-5-(morpholine-4-sulfonyl)-benzoic acid

To a solution of 3-Bromo-5-chlorosulfonyl-4-fluoro-benzoic acid (3.0 g) in dioxane/water (9/1 (v/v), 30 ml) was added DiPEA (5 ml) and morpholine (1.65 ml). After stirring for 2 h, the mixture was diluted with EtOAc and washed with 2 M aq. HCl. The organic layer was dried (Na$_2$SO$_4$) and concentrated in vacuo. Yield: 2.6 g.

(c). 3-Bromo-4-(2-methoxy-ethylamino)-5-(morpholine-4-sulfonyl)-benzoic acid

A solution of 3-Bromo-4-fluoro-5-(morpholine-4-sulfonyl)-benzoic acid (500 mg) in 2-methoxy-ethylamine was heated at 80° C. for 3 h. The mixture was dissolved in 2 M aq. NaOH and washed with EtOAc. The aqueous layer was acidified with 2 M HCl and extracted with EtOAc. The organic layer was dried (Na$_2$SO$_4$) and concentrated in vacuo. Yield: 575 mg.

(d). 3-Bromo-4-(2-methoxy-ethylamino)-5-(morpholine-4-sulfonyl)-benzaldehyde

To a solution of the product described in step c (571 mg) in THF was added BH$_3$.THF (4.5 ml, 1 M in THF). After stirring for 2 h at RT, aqueous work-up, extraction (EtOAc) and concentration in vacuo yielded the crude alcohol, which was dissolved in THF. MnO$_2$ (587 mg) was added and the mixture was stirred overnight. Filtration over decalite and concentration in vacuo gave the desired crude compound, which was purified by crystallization from diethyl ether. Yield: 243 mg.

(e). 4-[3-Bromo-4-(2-methoxy-ethylamino)-5-(morpholine-4-sulfonyl)-phenyl]-2-methyl-5-oxo-7-propyl-1,4,5,6,7,8-hexahydro-quinoline-3-carbonitrile A mixture of the product of step d (61 mg), 3-aminocrotonitrile (12.3 mg) and 5-propylcyclohexane-1,3-dione (23.1 mg) in ethanol (5 ml) was stirred at 80° C. for 17 h. The reaction mixture was concentrated in vacuo and the residue was purified by preparative HPLC (Method B). Yield: 57 mg. MS-ESI: [M+H]$^+$=607.3/609.3; HPLC: R$_t$=16.51 min. (diast. 1) R$_t$=16.83 min. (diast. 2) (method 1). Diast. ratio: 9:1

Example 32

4-[3-Bromo-4-(2-methoxy-ethylamino)-5-(pyrrolidine-1-sulfonyl)-phenyl]-2-methyl-5-oxo-7-propyl-1,4,5,6,7,8-hexahydro-quinoline-3-carbonitrile (a). 3-Bromo-4-fluoro-5-(pyrrolidine-1-sulfonyl)-benzoic acid To a solution of 3-Bromo-5-chlorosulfonyl-4-fluoro-benzoic acid (3.0 g) in dioxane/water (9/1 (v/v), 30 ml) was added DiPEA (5 ml) and pyrrolidine (1.55 ml). After stirring for 2 h, the mixture was diluted with EtOAc and washed with 2 M aq. HCl. The organic layer was dried (Na$_2$SO$_4$) and concentrated in vacuo. Yield: 2.3 g.

(b). 3-Bromo-4-(2-methoxy-ethylamino)-5-(pyrrolidine-1-sulfonyl)-benzoic acid

A solution of 3-Bromo-4-fluoro-5-(pyrrolidine-1-sulfonyl)-benzoic acid (500 mg) in 2-methoxy-ethylamine was heated at 80° C. for 3 h. The mixture was dissolved in 2 M aq. NaOH and washed with EtOAc. The aqueous layer was acidified with 2 M HCl and extracted with EtOAc. The organic layer was dried (Na$_2$SO$_4$) and concentrated in vacuo. Yield: 543 mg.

(c). 3-Bromo-4-(2-methoxy-ethylamino)-5-(pyrrolidine-1-sulfonyl)-benzaldehyde

To a solution of the product described in step c (542 mg) in THF was added BH$_3$.THF (4.0 ml, 1 M in THF). After stirring for 2 h at RT, aqueous work-up, extraction (EtOAc) and concentration in vacuo yielded the crude alcohol, which was dissolved in THF. $MnO_2$ (578 mg) was added and the mixture was stirred overnight. Filtration over decalite and concentration in vacuo gave the desired crude compound, which was purified by crystallization from diethyl ether. Yield: 294 mg.

(d). 4-[3-Bromo-4-(2-methoxy-ethylamino)-5-(pyrrolidine-1-sulfonyl)-phenyl]-2-methyl-5-oxo-7-propyl-1,4,5,6,7,8-hexahydro-quinoline-3-carbonitrile A mixture of the product of step c (59 mg), 3-aminocrotonitrile (12.3 mg) and 5-propylcyclohexane-1,3-dione (23.1 mg) in ethanol (5 ml) was stirred at 80° C. for 17 h. The reaction mixture was concentrated in vacuo and the residue was purified by preparative HPLC (Method B). Yield: 57 mg. MS-ESI: $[M+H]^+$=591.3/593.3; HPLC: $R_t$=18.43 min. Diast. ratio: 9:1

Example 33

Agonistic Activity of Compounds at the Human FSH Receptor Expressed in CHO Cells Agonist activity of the compounds at the human FSH receptor was tested in Chinese Hamster Ovary (CHO) cells stably transfected with the human FSH receptor and cotransfected with a cAMP responsive element (CRE)/promotor directing the expression of a firefly luciferase reporter gene. Binding of the compound to the Gs-coupled FSH receptor will result in an increase of cAMP, which in turn will induce an increased transactivation of the luciferase reporter construct. The luciferase activity was quantified using a luminescence counter. The compounds were tested in the concentration range of 0.1 nM to 10 µM. This assay was used to determine the $EC_{50}$ (concentration of test compound causing half-maximal (50%) luciferase stimulation) and efficacy of the compounds compared to recombinant human FSH. For this, the software program XLfit (Excel version 2.0, built 30, ID Business Solutions Limited) was used.

Compounds of all examples had an activity ($EC_{50}$) of less than $10^{-6}$ M. Some of the compounds, such as those of examples 2, 3, 5, 6, 12, 13, 17, 20, 22, 23, 24, 26, 28, 29, 30, 31 and 32, showed an $EC_{50}$ of less than $10^{-8}$ M.

What is claimed is:
1. A 2-methyl-4-phenyl-5-oxo-1,4,5,6,7,8-hexahydroquinoline derivative according to Formula 1,

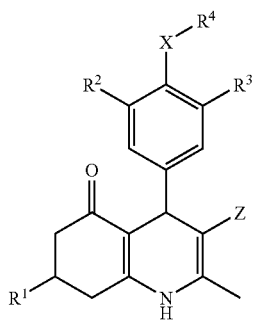

Formula I wherein $R^1$ is (1-6C)alkyl, (2-6C)alkenyl or (2-6C)alkynyl;

$R^2$ is halogen;

$R^3$ is $SO_2NR^5R^6$ or (1-4C)alkoxy, optionally substituted with one of more fluorine atoms;

X is O or $NR^7$;

$R^4$ is $R^8$—(2-8C)alkyl, $R^8$—(3-8C)alkenyl, $R^8$—(3-8C)alkynyl or $R^8$—(2-4C)alkoxy-(2-4C)alkyl;

Z is CN or $NO_2$;

$R^5$ and $R^6$ are independently H or (1-4C)alkyl; or $R^5$ together with $R^6$ and the N to which they are bonded form a 3-8 membered saturated ring optionally containing a further heteroatom selected from O and S;

$R^8$ is OH, (1-4C)alkoxy, $NH_2$; $NR^9C(O)R^{11}$, $NR^9SO_2R^{11}$ or $C(O)NR^9R^{10}$;

$R^7$ and $R^9$ are independently H or (1-4C)alkyl;

$R^{10}$ is (1-4C)alkyl, (1-4C)alkoxy(1-4C)alkyl, or phenyl(1-4C)alkyl or (2-5C)heteroaryl(1-4C)alkyl, both optionally substituted on the (hetero)aromatic ring with one or more substituents selected from OH, $NH_2$, halogen, $NO_2$, $CF_3$, CN, (1-4C)alkyl, (1-4C)alkoxy and (di)(1-4C)alkylamino;

$R^{11}$ is (1-4C)alkyl, (2-4C)alkenyl, (2-4C)alkynyl, (1-4C)alkoxy(1-4C)alkyl, (3-6C)-cycloalkyl, (1-4C)alkoxy, (di)(1-4C)alkylamino, or phenyl or (2-5C)heteroaryl, both optionally substituted on the (hetero)aromatic ring with one or more substituents selected from OH, $NH_2$, halogen, $NO_2$, $CF_3$, CN, (1-4C)alkyl, (1-4C)alkoxy and (di)(1-4C)alkylamino; or a pharmaceutically acceptable salt thereof.

2. The 2-methyl-4-phenyl-5-oxo-1,4,5,6,7,8-hexahydroquinoline derivative of claim 1, wherein X is O.

3. The 2-methyl-4-phenyl-5-oxo-1,4,5,6,7,8-hexahydroquinoline derivative of claim 1, wherein $R^1$ is (1-6C)alkyl.

4. The 2-methyl-4-phenyl-5-oxo-1,4,5,6,7,8-hexahydroquinoline derivative of claim 1, wherein $R^2$ is Cl, Br or I.

5. The 2-methyl-4-phenyl-5-oxo-1,4,5,6,7,8-hexahydroquinoline derivative of claim 1, wherein Z is CN.

6. The 2-methyl-4-phenyl-5-oxo-1,4,5,6,7,8-hexahydroquinoline derivative of claim 1, wherein $R^3$ is $SO_2NR^5R^6$.

7. A pharmaceutical composition comprising a 2-methyl-4-phenyl-5-oxo-1,4,5,6,7,8-hexahydroquinoline derivative of claim 1 or a pharmaceutically acceptable salt thereof, and pharmaceutically suitable auxiliaries.

* * * * *